United States Patent [19]
Kaji

[11] Patent Number: 6,033,426
[45] Date of Patent: Mar. 7, 2000

[54] ACCESS DEVICE FOR SURGICAL TREATMENT

[75] Inventor: Kunihide Kaji, Hachioji, Japan

[73] Assignee: Olympus Optical Co., Ltd., Tokyo, Japan

[21] Appl. No.: 09/122,523

[22] Filed: Jul. 24, 1998

[30] Foreign Application Priority Data

Jul. 29, 1997 [JP] Japan ................................. 9-203114
Jul. 14, 1998 [JP] Japan ................................ 10-198625

[51] Int. Cl.⁷ ................................................ A61B 17/08
[52] U.S. Cl. ........................... 606/213; 600/207; 604/174
[58] Field of Search ........................ 606/1, 213; 604/174, 604/256; 600/207

[56] References Cited

U.S. PATENT DOCUMENTS

| | | | |
|---|---|---|---|
| 5,366,478 | 11/1994 | Brinkerhoff et al. | 606/207 |
| 5,514,133 | 5/1996 | Golub et al. | 606/1 |
| 5,522,791 | 6/1996 | Leyva | 606/213 |
| 5,853,395 | 12/1998 | Crook et al. | 604/174 |
| 5,906,577 | 5/1999 | Bean et al. | 600/207 |

FOREIGN PATENT DOCUMENTS

WO 96/10963  4/1996  WIPO.

*Primary Examiner*—Michael Buiz
*Assistant Examiner*—Vy Q. Bui
*Attorney, Agent, or Firm*—Frishauf, Holtz, Goodman, Langer & Chick P.C.

[57] ABSTRACT

The access device according to the present invention is an access device for connecting an interior of a living body to the exterior thereof and for inserting an object into the living body in a sealed state, the device comprising a communication body to be set in tight contact with an incised part of a wall of the living body, for pushing open the incised part, thereby to allow an interior of the living body to communicate with the exterior of the living body, a first valve attached and sealed to communication body, and a second valve attached and sealed to the communication body and adapted to be placed inside or outside the living body, the second valve being located closer to the living body than the first valve while placed outside the living body, wherein the first valve has a valve main body made of an elastic material and an insertion part provided on the valve main body, capable of elastically deforming when the object is inserted into the insertion part, thereby to allow the object to be inserted into the living body in the sealed state, and the second valve has a plurality of film bodes formed of an elastic material and attached on an inside surface of the communication body, each of the film bodies has a contact surface, is bent toward the interior of the living body approximately in the axial direction of the communication body and is adapted to contact the adjacent film bodies at the contact surface.

29 Claims, 20 Drawing Sheets

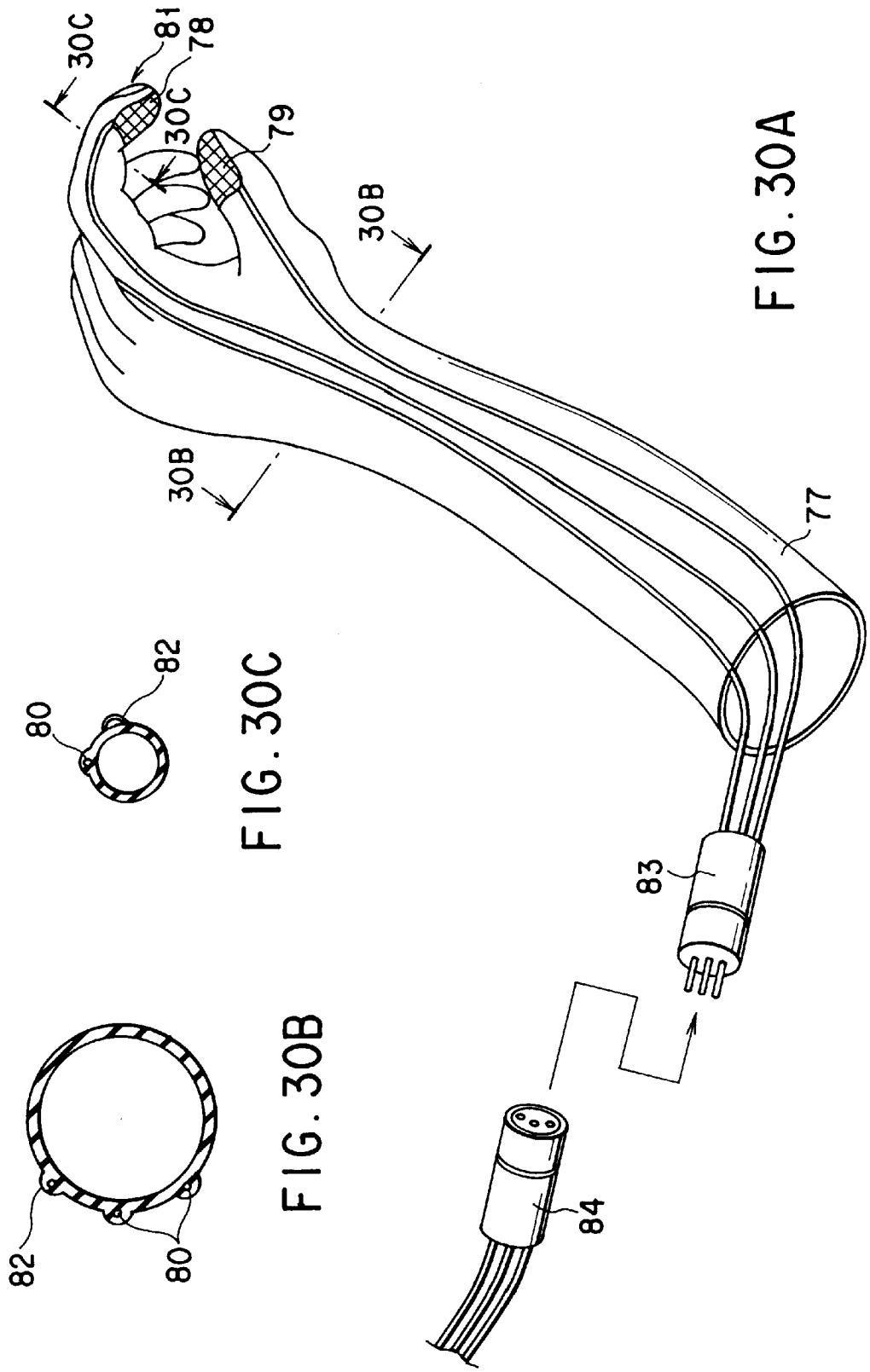

ACCESS DEVICE FOR SURGICAL TREATMENT

BACKGROUND OF THE INVENTION

The present invention relates to an access device for a surgical treatment which device is used in a surgical operation under an endoscope and for forming an inlet to the inside of a body from the outside thereof.

Today, as a treatment which is known as the surgical treatment of celiac organs, two methods are given; a treatment under a direct observation by means of the sectioning of the abdomen (celiotomy), and the surgical treatment under observation using the endoscope. Although the celiotomy is the most standard treatment method, there arises a problem in that it is required that the abdomen must be largely sectioned in the celiotomy so that the invasion on the side of the patient is large, pains after the treatment prolongs, a long-term hospitalization is required, or anastomosis of the tissue with respect to the sectioned part is generated. On the other hand, the surgical treatment under an endoscope is a treatment in which a treatment device having a long shaft is allowed to pass through a small hole opened in the body while the endoscope image displayed on the monitor is being observed. Consequently, the treatment has an advantage in that the invasion on the side of the patients is small, the treatment is excellent in terms of esthetic aspect, and, at the same time, pains after the treatment are not strong, an early recovery from the damage and an early discharge from the hospital can be made possible. However, from the viewpoint of the surgeon, the surgical treatment under the endoscope requires many techniques such as an operation of forceps and the like. Thus, it is possible to say that the treatment is a method having a considerable peculiarity as compared with the celiotomy. Out of various characteristics, the absence of the tactus constitutes a large factor which makes this treatment method very difficult. For the surgeon in charge of the treatment the tactus constitutes means for obtaining a large amount of useful information on blood vessels and the diagnosis of tissues in the case of tumors or the like which information cannot be obtained in the monitor. The tactus enables the surgeon to administer the treatment in a smooth manner. Thus, it is possible to say that this is a large advantage of the celiotomy.

On the other hand, as a method which compensates for the disadvantages of the two surgical treatments and which doubles the advantages of the aforementioned two surgical treatments, there is proposed a method in which a hand of the surgeon is inserted into an abdominal cavity to treat the abdomen by means of the endoscope with an auxiliary help of the hand of the surgeon. For example, U.S. Pat. No. 5,366,478 discloses a method for holding the air-tight state of the inside of the body at the time of inserting the hand into the body through a transition section or at the time of removing the hand through the transition section from the inside of the body by arranging two donut-shaped balloons inside and outside of the body and swelling the balloons. According to the method, the abdomen can be treated with the inserted hand while a cavity is secured with gas which is sent into the abdomen in the same manner as the conventional surgical treatment under the endoscope. As a consequence, the treatment which cannot be accomplished in the surgical treatment under the endoscope can be administered in a safe manner and in a short time.

Furthermore, U.S. Pat. No. 5,514,133 discloses a method for holding the air-tight state of the body at the time of the insertion and the removal of the hand by sandwiching the abdominal wall with two plates which are connected with bellows, and by arranging a flap valve-shaped valve in a channel which is defined by the two plates. Furthermore, U.S. Pat. No. 5,522,791 discloses a technique for engaging in the air-tight manner a circular elastic member with a sectioned part and, at the same time, providing a sealing member on a sleeve which extends toward the outside from the circular elastic member thereby sealing a sleeve and an arm inserted into the sleeve with this sealing member. Furthermore, PCT WO 96/10963 discloses a technique for providing on a sleeve a first and a second open part which can be closed, and preventing gas inside of the body from leaking to the outside by closing the open parts.

However, in the technique which is disclosed in U.S. Pat. No. 5,366,478, there is provided only one sealing part so that gas leakage is generated at the time of inserting the hand into the body. Besides, in the case where the hand is not inserted into the inside of the body, an inside hole of the donut-shaped balloon must be completely sealed, and it is structurally difficult to hold the air-tight state. Furthermore, there is considered a disadvantage in that the arm is fastened with the balloon, and a cavity to be treated is narrowed down because the balloon is large.

Furthermore, in the technique which is disclosed in U.S. Pat. No. 5,514,133, there is a disadvantage in that the bellows and the valve are located on the sectioned part so that the length of the sectioned part becomes longer than necessary. Furthermore, in this technique, a sufficient space is needed for opening and closing of the flap-shaped valve so that the cavity to be treated is narrowed down as a consequence. Furthermore, this technique has a disadvantage in that the structure thereof is complicated and the setting also becomes troublesome.

Furthermore, in the techniques which are disclosed in U.S. Pat. No. 5,522,791 and PCT WO 96/10963, there is provided a sleeve which extends toward the outside of the body so that there is a problem in that force is received which pushes back the arm constantly to the outside under the pneumoperitoneum, and the pneumoperitoneum pressure abruptly rises by the insertion of the arm into the abdominal cavity. Besides, this technique is structurally difficult, and a very complicated procedure must be taken to put the hand into and out of the body so that the technique is not appropriate in a practical usage.

As described above, in the prior art, it is difficult to completely seal the sectioned part having a large aperture which allows the insertion of the hand. Consequently, it is necessary from now on to consider a peculiar valve structure which is completely different from a valve of a surgical instrument (called trocar) for the conventional surgical treatment under the endoscope.

BRIEF SUMMARY OF THE INVENTION

An object of the invention is to provide an access device for a surgical treatment wherein an object to be inserted (for example, a hand or an arm) can be easily allowed to go into and out of an abdominal cavity with a simple structure, and the air-tight state of the abdominal cavity can be completely held at the time when the object to be inserted is inserted into the abdominal cavity, and at the time when the object is removed out of the abdominal cavity, and still, the object to be inserted (for example, a hand or an arm) is not fastened.

The object of the invention is attained with the following access device for the surgical treatment. In other words, this access device of the invention is an access device for connecting an interior of a living body to the exterior thereof and for inserting an object into the living body in a sealed state, said device comprising:

a communication body to be set in tight contact with an incised part of a wall of the living body, for pushing open the incised part, thereby to allow an interior of the living body to communicate with the exterior of the living body;

a first valve attached and sealed to communication body; and a second valve attached and sealed to the communication body and adapted to be placed inside or outside the living body, said second valve being located closer to the living body than the first valve while placed outside the living body;

wherein the first valve has a valve main body made of an elastic material and an insertion part provided on the valve main body, capable of elastically deforming when the object is inserted into the insertion part, thereby to allow the object to be inserted into the living body in the sealed state, and the second valve has a plurality of film bodies formed of an elastic material and attached on an inside surface of the communication body, each of the film bodies has a contact surface, is bent toward the interior of the living body approximately in the axial direction of the communication body and is adapted to contact the adjacent film bodies at the contact surface.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 30A is a perspective view of gloves for the operation used at the time of administering the treatment in the abdominal wall.

FIG. 30B is a sectional view taken along line 30B—30B of FIG. 30A.

FIG. 30C is a sectional view taken along line 30C—30C of FIG. 30A.

FIG. 36 is a sectional view showing a state in which the arm is inserted further into the back of the abdominal wall from the state shown in. FIG. 35.

DETAILED DESCRIPTION OF THE INVENTION

Figure 1:
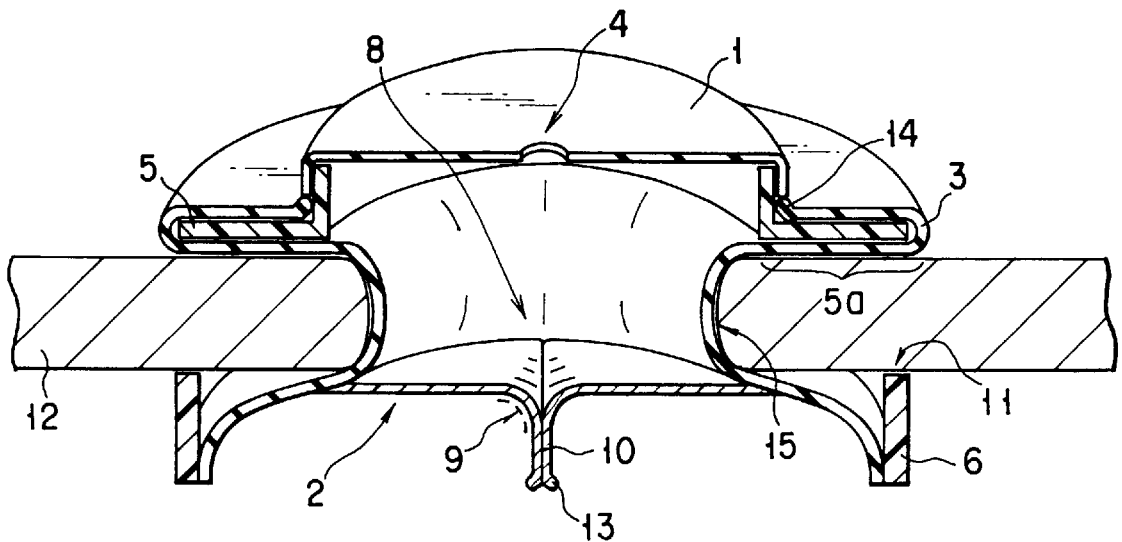
FIG. 1 is a perspective view showing a state in which an access device for a surgical treatment according to a first embodiment of the present invention is attached on an abdominal wall, the view being accompanied by a partial cross section of the access device.

Each of embodiments of the present invention will be explained by referring to the drawings.

FIGS. 1 through 7A and 7B show a first embodiment of the present invention. FIG. 1 shows a state in which the access device for a surgical treatment according to an embodiment of the present invention is attached on the abdominal wall. As shown in FIG. 1, the access device has a first valve 1 located on the side outside of the body, and a second valve 2 located on the side inside of the abdominal cavity. The first valve 1 and the second valve 2 are connected to each other with a thin-film-like sleeve (communication body) 3 which is formed of, for example, a thin and expandable latex rubber.

The first valve 1 is such that a hole 4 is opened in a central part of a circular-shaped elastic thin film for inserting a hand of the surgeon. The diameter of the hole 4 is smaller than the thickness of the arm of the surgeon. The hole 4 is expanded by the insertion of the hand and the first valve 1 closely adheres to a circumference of the hand or the arm thereby making it possible to prevent a gas leakage. The first valve 1 is fixed to a half solid sleeve fixing member (first support part) 5 having a flange part 5a, and a side of the sleeve 3 which side is arranged on the outside of the body is fit into the flange part 5a and is fixed thereto.

The sleeve 3 is located on a part of the sectioned part (incised part) 15 of the abdominal wall 12 so that the sectioned part 15 is expanded in such a manner that the hand can be easily inserted thereinto, and this part is protected which contributes toward the prevention of causing damage to the sectioned part 15, and toward the prevention of bleeding and infection. In addition, as compared with the case in which a solid tube is used as a channel, a blood flow around the sectioned part 15 is not prevented so that the sectioned part 15 is not expanded by force.

A half-solid removal prevention ring (a second support part) 6 connected to the other end of the sleeve 3 is inserted into the abdominal cavity thereby serving as a function of preventing the removal of the sleeve 3 from the abdominal. Two half-circular-shaped elastic thin films are extended in the central direction from the inside surface of the sleeve 3 in the vicinity of the connection part of the sleeve 3 and the ring 6 and are folded back (a fold-back part 9) in an axial direction of the sleeve 3 at a diameter part thereby forming a contact surface 10. The end part 13 becomes somewhat thicker in thickness in a straight-line manner.

The first valve 1 serves to secure an air-tight state at the time of inserting the hand thereinto, while the second valve 2 serves to secure the air-tight state at the time of not inserting the hand thereinto. The first and the second valve 1 and 2 are arranged with a certain distance (for example, the distance is larger than the size of the fist) between the two so that gas leakage can be prevented at the time of inserting the hand thereinto and removing the hand therefrom. In other words, when the first valve 1 and the second valve 2 are separated from each other in a distance which is larger than a predetermined distance, the second valve 2 is opened with the hand after the hand is inserted into the first valve 1 and the first valve 1 is sealed. Consequently, when the hand is inserted into the valves or is removed from the valves, gas leakage from the abdominal cavity can be prevented.

Figure 2A:
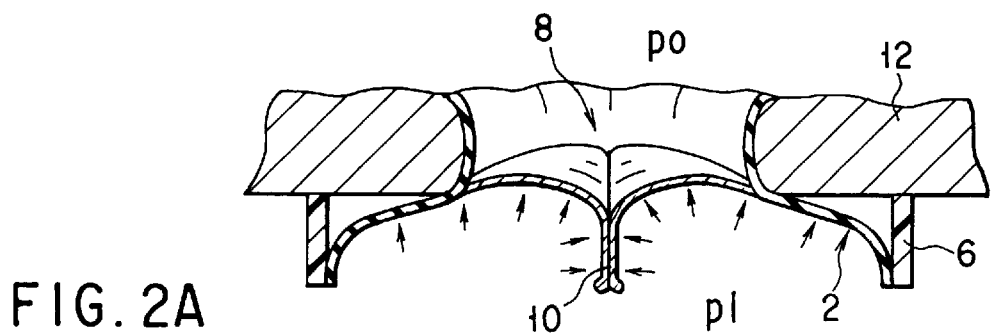
FIG. 2A is a sectional view showing a completely sealed state of a second valve of the access device shown in FIG. 1.
Figure 2B:
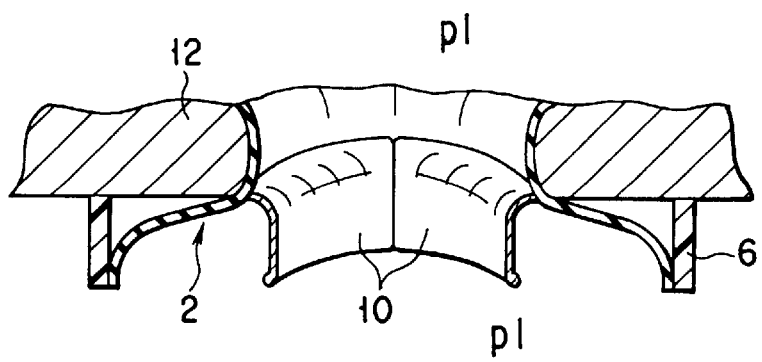
FIG. 2B is a sectional view showing a state in which an object to be inserted is inserted into the second valve of the access device shown in FIG. 1.

FIGS. 2A and 2B show a function of the second valve 2. FIG. 2A shows a state in which the air-tight state is held under pneumoperitoneum. Since the inside pressure (pneumoperitoneum pressure p1) of the second valve 2 is higher than the outside pressure (p0) of the second valve 2, the thin film of the second valve 2 is swollen with the inside pressure, and the contact surface 10 thereof receives force in a direction of closely adhering to each other thereby making it possible to completely prevent the gas leakage from a slit-like open part 8. On the other hand, in the state in which the hand is inserted into the second valve 2 and the valve 2 is opened, the inside and the outside pressure (p1) of the second valve 2 become equal to each other (refer to FIG. 2B) with the result that the force which is received by the hand from the second valve 2 is only an elastic force which is caused by the deformation of the contact surface 10 (at this time, the air-tight state with the outside of the body is held with the first valve 1). The thin film of the second valve 2 is more affected by the pressure when the film is thinner. Thus, there is an advantage in that when the film is thinner, the thin film can be more effectively sealed, and, in addition, the force fastening the arm becomes very small in the open state.

Incidentally, the structure of the second valve 2 is useful not only as a port for inserting the hand therewith, but also as a trocar valve which is generally used in an operation under an endoscope. In addition, the valve 2 can be used by inserting a forceps having a long shaft from the access device installed for inserting the hand by mating the hole 4 of the first valve 1 with the forceps having the long shaft.

Figure 3:
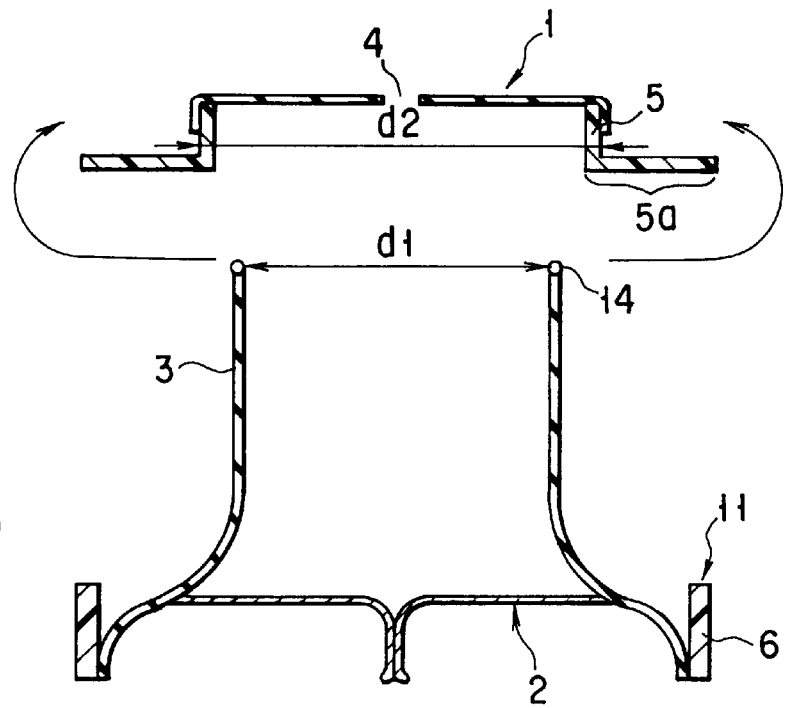
FIG. 3 is a sectional view showing a method for fixing a sleeve of the access device to a sleeve fixing member shown in FIG. 1.
Figure 4A:
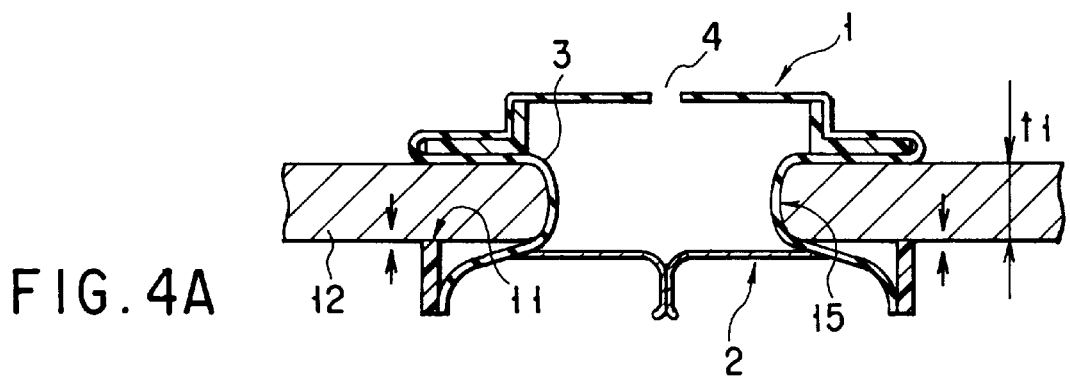
FIG. 4A is a sectional view showing a state in which the access device shown in FIG. 1 is attached on a thin abdominal wall.
Figure 4B:
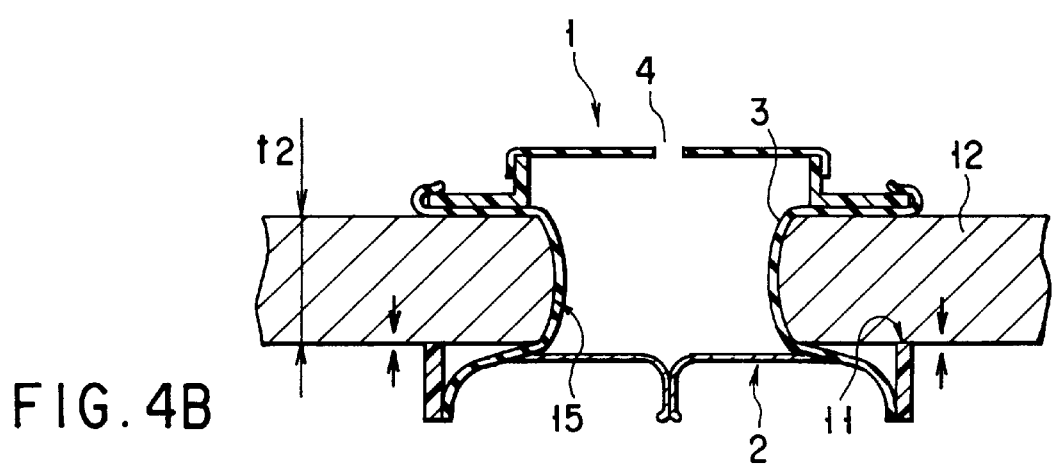
FIG. 4B is a sectional view showing a state in which the access device shown in FIG. 1 is attached on the thick abdominal wall.

FIGS. 3, 4A and 4B show a method for fixing a sleeve 3 and a sleeve fixing member 5. As shown by an arrow in FIG. 3, a sleeve end part 14 and a flange part 5a can be assembled with each other by covering the flange part 5a with the sleeve end part 14. Since the diameter d1 of the sleeve end part 14 is smaller than the outside diameter d2 of a mouthpiece part of the sleeve fixing member 5, the sleeve end part 14 after the attachment is moved in a direction in which the sleeve end part 14 is shrunken on the flange part 5a, namely, the sleeve 3 is naturally fit into the flange part 5a and is moved in a direction of diminishing a distance between the removal preventing ring 6 and the sleeve fixing member 5.

FIGS. 4A and 4B are views showing a state in which the sleeve 3 and the sleeve fixing member 5 are attached on different abdominal walls (wall thickness ... t1 and t2). With a covering end of the flange part 5a and the expandability of the sleeve 3, the sleeve 3 and the flange part 5 can be surely attached so as to sandwich the abdominal wall 12 thereby conforming to any of the abdominal wall thickness. Consequently, since the sealing surface 11 of the removal prevention ring 6 closely adheres to the abdominal wall (as shown by arrows in FIGS. 4A and 4B), a gas leakage between the sectioned part 15 and the sleeve 3 is not generated.

Figure 5:
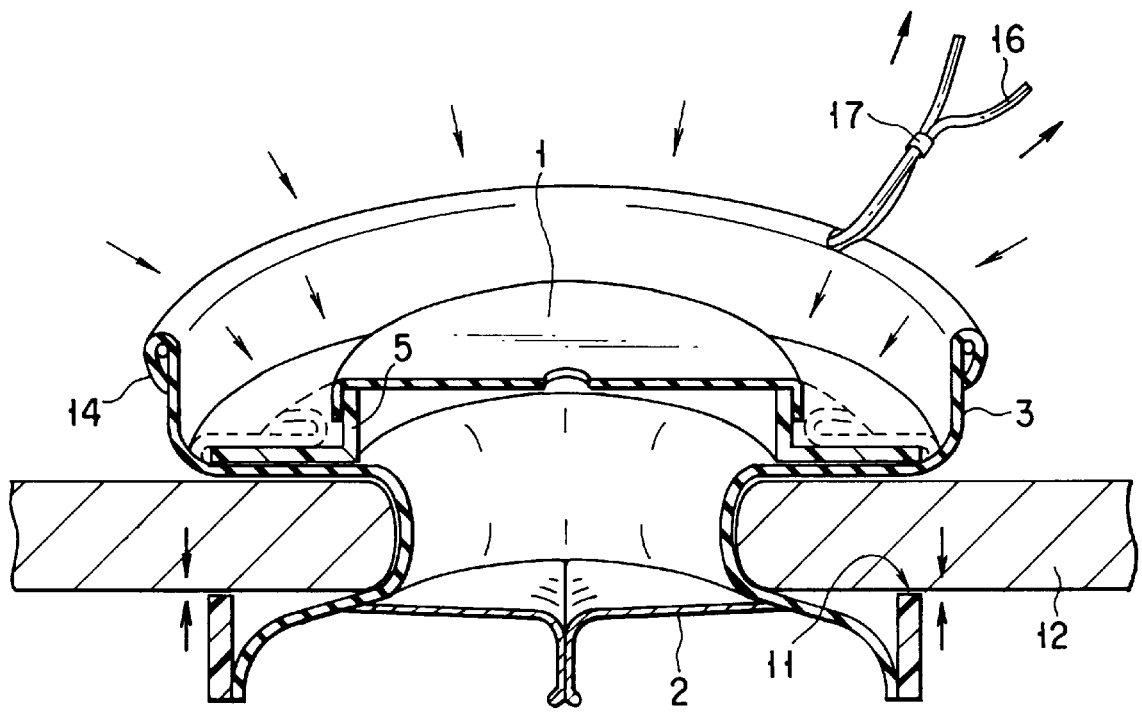
FIG. 5 is a perspective view showing another example of the method for fixing the sleeve of the access device to the sleeve fixing member shown in FIG. 1, the view being accompanied by a partial cross section of the access device.

FIG. 5 shows another method for fixing the sleeve 3 and the sleeve fixing member 5. The sleeve end part 14 is folded back, a wire 16 is arranged therein, the wire 16 is fastened, and the sleeve end part 14 is twisted like a money pouch (a part shown by a broken line in FIG. 5) with the result that the sealing surface 11 is allowed to closely adhere to the abdominal wall 12 in an active manner. Such a structure is adopted which makes it possible to conform to an abdominal wall thickness in a wider scope.

Figure 6:
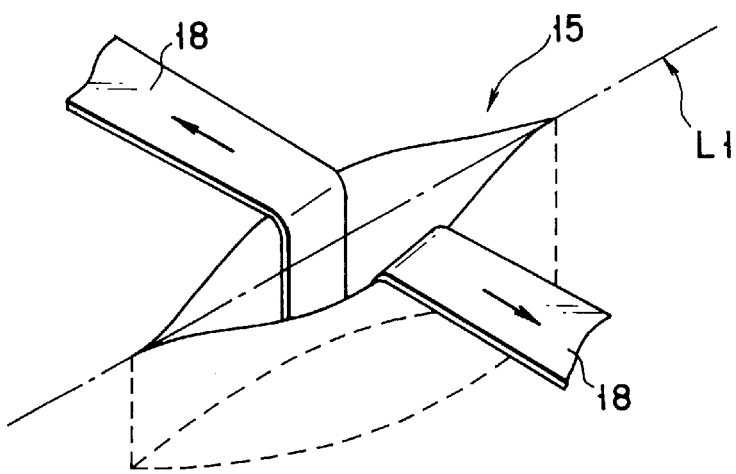
FIG. 6 is a perspective view showing a state in which a sectioned part is pushed open for setting the second valve in the abdominal wall.
Figure 7A:
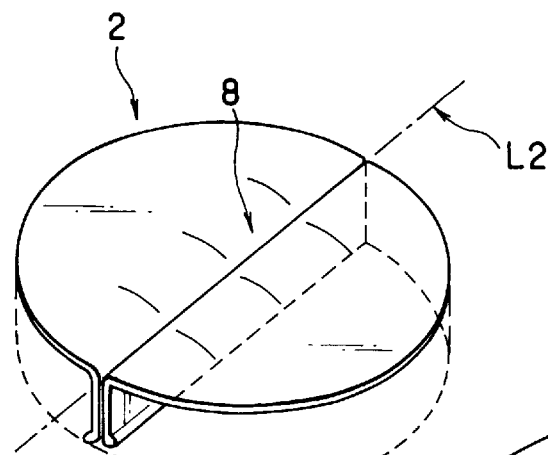
FIG. 7A is a perspective view showing a state in which the second valve is set in the abdominal wall.
Figure 7B:
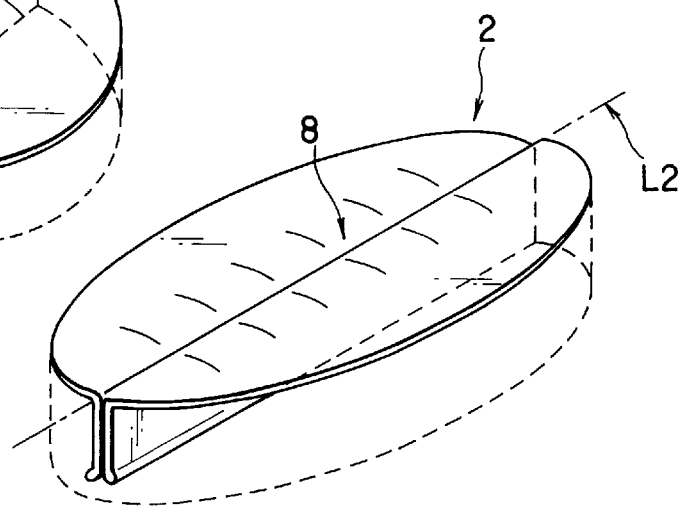
FIG. 7B is a perspective view showing a state in which the second valve is set in the abdominal cavity.
Figure 8:
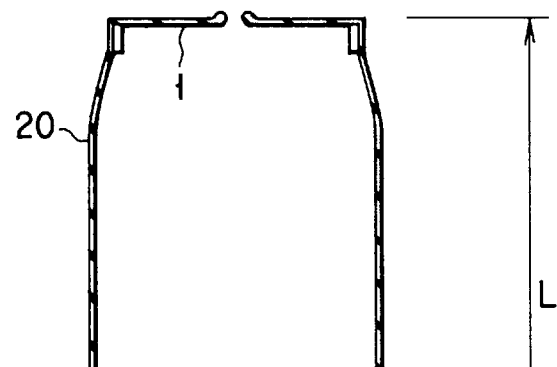
FIG. 8 is a sectional view showing a state in which the access device for the surgical treatment according to a second embodiment of the invention is attached on the abdominal wall.

FIGS. 6, 7A and 7B show a state in which the second valve 2 is actually set on the abdominal wall 12. As shown in FIG. 6, the section is made in a straight line, and the length of the section is set to a minimum length required for inserting the hand therewith. This sectioned part is expanded with an unguiculus 18 and thereafter the half-solid removal preventing ring 6 is inserted into the abdominal cavity with the ring 6 deformed. At this time, the sectioned part 15 is expanded in an oblong-like configuration. However, as described above, when the abdominal wall 12 is sandwiched with the sleeve fixing member 5 and the removal preventing ring 6, the half-solid removal prevention ring 6 and the second valve 2 are also deformed in an oblong-like configuration in the same manner (refer to FIG. 7B). Since the deformation direction of the second valve 2 is determined by the sectioning direction L1, the sectioning direction L1 is aligned approximately with the direction L2 of the slit-like open part 8 in order that the second valve 2 functions. By doing so, a secured sealing function can be obtained irrespective of the size of the thickness of the abdominal wall and the length of the sectioned part (when the directions are different from each other, the slit-like open part 8 is constantly opened and does not function in an appropriate manner).

As explained above, the access device according to the embodiment has a first valve 1 and a second valve 2. In the state in which the object is inserted into the abdominal cavity, the first valve 1 holds the air-tight state while the second valve 2 holds the air-tight state when the object is not inserted into the abdominal cavity. Furthermore, the second valve 2 is formed of a plurality of elastic thin films which are extended in a direction of the central part from the wall surface inside of the access device. At a radius position where every one of the thin films contacts each other, each of the thin films is folded back in an axial direction of the access device with the result that a slit-like open part 8 is formed, and the folded back part 9 forms a contact surface 10. Consequently, in the access device according to the embodiment of the invention, the air-tight state can be held both in the state in which the object is inserted into the abdominal cavity and in the state in which the object is removed from the abdominal cavity. Particularly, in the state in which the object is removed therefrom, the contact surface 10 receives force in a direction of closely adhering to each other with the inside pressure of the abdominal cavity. Thus, the air-tight state can be completely held in the abdominal cavity with a simple structure. Furthermore, since the second valve 2 is formed of a thin film, the valve can be easily deformed in configuration. Consequently, there is an advantage in that a volume of insertion or removal force at the time of inserting the object therewith or removing the object therefrom becomes small. Furthermore, the access device is useful in the protection of the sectioned part 15.

Furthermore, the access device according to the embodiment is such that the thickness of the end part 13 of the folded back part 9 of the thin film which forms the contact surface 10 becomes larger than the thickness of the film. Consequently, it is possible to prevent the thin film of the second valve 2 from being swollen more than needed at an end part 13 thereof with the inside pressure of the abdominal cavity. In other words, since the length of the folded back part 9 can be made smaller (the contact area thereof can be made smaller), the volume of the insertion and detachment force can be made smaller and the structure can be made to a compact size.

In addition, in the access device according to the embodiment, the distance between the first valve 1 and the second valve 2 is set to a level larger than the fist of the surgeon. Consequently, air leakage at the time of the insertion of the hand can be prevented. In other words, the air-tight state in the abdominal cavity is held with the second valve 2 until the fist is inserted into the access device. After the fist is inserted, the first valve 1 seals the circumference of the wrist with the result that the air leakage caused by the insertion of the hand can be completely prevented.

FIGS. 8 through 11A and 11B show a second embodiment of the present invention. Only points of the second embodiment which are different from points in the first embodiment will be explained hereinbelow. On a surface of the removal prevention ring 6 which surface closely adheres to the abdominal wall 12, a ring-like sealing member 19 which is formed of a silicone rubber or the like is arranged to secure the air-tight state of this part. On the sleeve fixing member 5, a thin-film-like sleeve 20 having a length L is detachably attached and the first valve 1 is arranged on the end part of the sleeve 20. The length L of the sleeve 20 approximately conforms to a length extending from the elbow over to the hand.

Figures 9A, 9B, 9C:
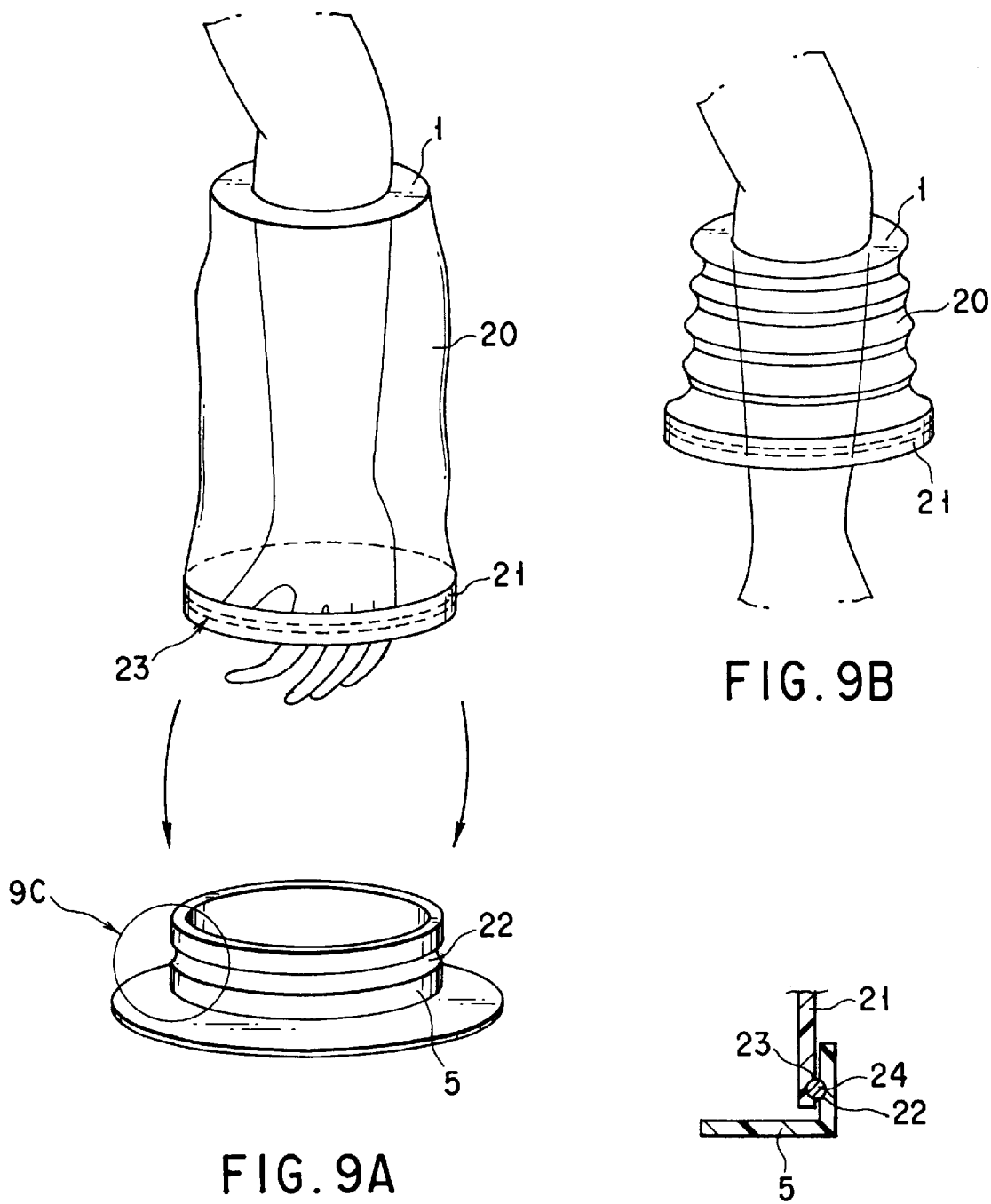
FIG. 9A is a perspective view showing a state in which the access device for the surgical treatment shown in FIG. 8 is assembled.
FIG. 9B is a perspective view showing a usage state of the access device for the surgical treatment shown in FIG. 8.
FIG. 9C is a sectional view of a part 9C shown in FIG. 9A.

FIGS. 9A to 9C show a state of the access device at the time of the usage thereof. The first valve 1 is attached on the arm, while the sleeve 20 is pushed up to the elbow as shown in FIG. 9B when the surgeon uses his hand outside of the body. As a consequence, the movement of the hand does not cause any trouble to the work of the surgeon thereby enabling the surgeon to carry out his work. On the other hand, since the air-tight state of the abdominal cavity is held with the second valve 2 fixed to the abdominal wall 12, the same observation and treatment as the normal operation under the endoscope can be made possible.

When the treatment in the abdominal cavity is administered by the insertion of the hand, the sleeve 20 is expanded as shown in FIG. 9A and the fixing ring 21 provided at the end part of the sleeve 20 is connected to the sleeve fixing member 5 with the result that the hand can be inserted into the abdominal cavity without leaking the gas in the abdominal cavity to the outside thereof. In the aforementioned structure, the first valve 1 is constantly attached on the elbow part with the result that the valve 1 is not required to correspond to the thickness extending from the wrist over to the elbow thereby making it possible to attach the valve 1 for a long time under more appropriate fastening force. Furthermore, when the length of the sleeve 20 is set to a length more than a predetermined length (for example, the length extending from the wrist over to the elbow), the hand is inserted into the first valve 1, and the first valve 1 is sealed followed by opening the second valve 2 by the hand. Consequently, when the hand is inserted thereinto or the hand is removed therefrom, the gas leakage can be prevented.

Figure 10:
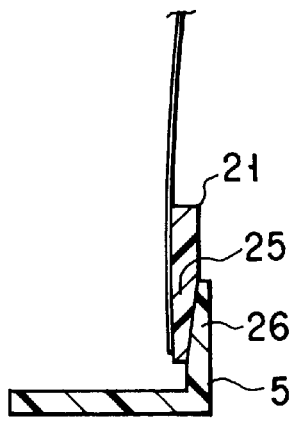
FIG. 10 is a sectional view showing a first modification of a connection state between a fixing ring of the sleeve and the sleeve fixing member.
Figure 11A:
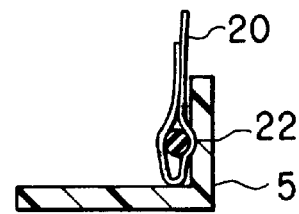
FIG. 11A is a sectional view showing a second modification of the connection state between the fixing ring of the sleeve and the sleeve fixing member.
Figure 11B:
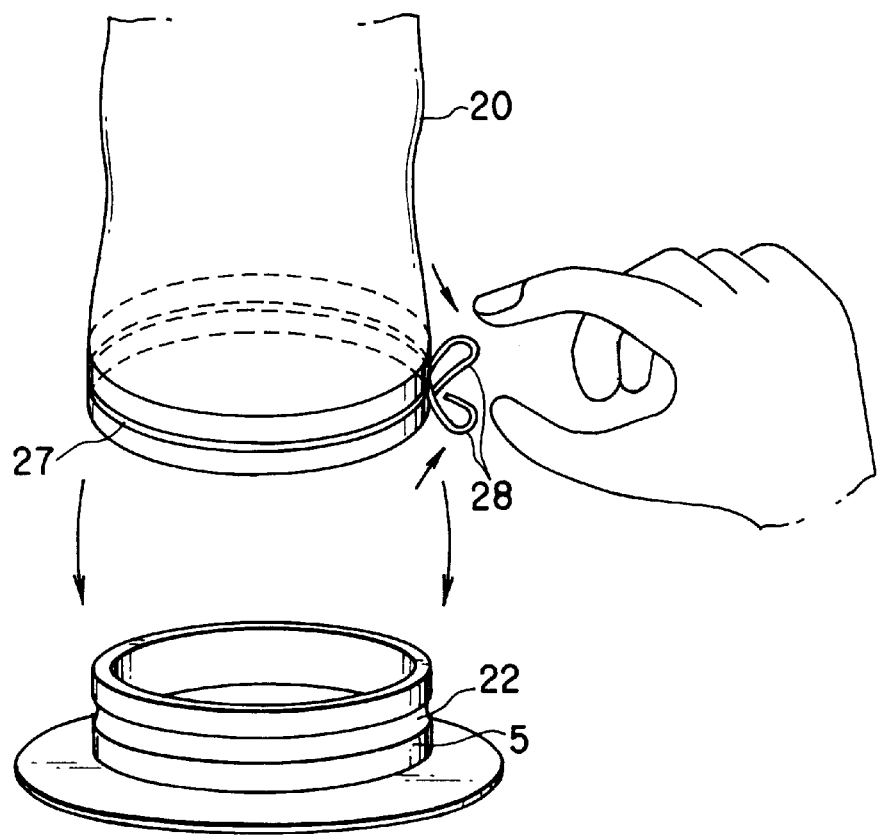
FIG. 11B is a perspective view showing a second modification of the connection state between the fixing ring of the sleeve and the sleeve fixing member.

The fixing ring 21 and the sleeve fixing member 5 are connected with a groove 22 provided on an outside circumference of the sleeve fixing member 5, an O-ring groove 23 provided on an inside circumference of the fixing ring 21, and an O-ring 24 arranged in the groove 23 as shown in FIG. 9A. On top of that, as shown in FIG. 10, the fixing ring 21 and the sleeve fixing member 5 may be connected with tapered fitting parts 25 and 26 provided on the outside surface of the fixing ring 21 and on the inside surface of the sleeve fixing member 5. As shown in FIGS. 11A and 11B. a device for the connection of the fixing ring 21 and the sleeve fixing member 5 may be of a type such that the end part of the sleeve 20 is folded back to expand an inside diameter of an elastic ring 27 which is formed of a stainless wire or a super-elastic alloy which is arranged in the inside of the end part of the sleeve 20 and which has a spring characteristic (there is shown an example in which the elastic ring 27 is expanded by moving a clamp 28 in a direction of an arrow to be attached on the flange part 5a followed by being relieved to be attached).

Figure 12:
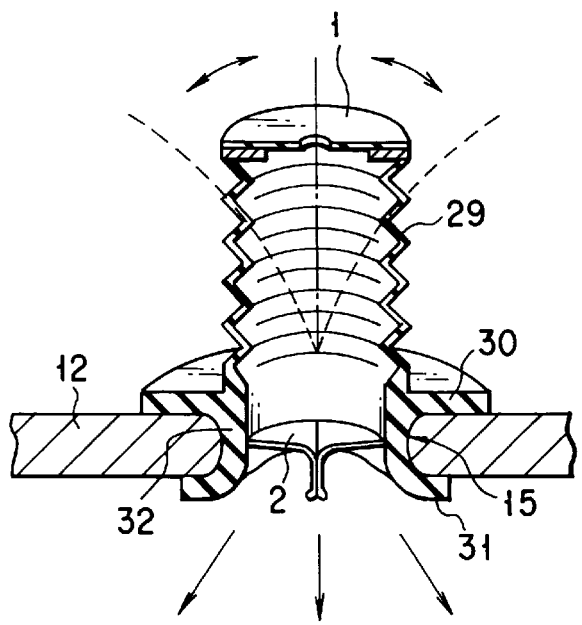
FIG. 12 is a perspective view showing a state in which the access device for the surgical treatment according to a third embodiment of the invention is attached on the abdominal wall, the view being accompanied by a partial cross section of the access device.

FIGS. 12 through 14A and 14B show a third embodiment of the present invention. Only points which are different from the points in the first embodiment will be explained hereinbelow. As shown in FIG. 12, the access device according to the third embodiment has a flange (first support part) 30 on the side outside of the body and a flange (second support part) 31 on the side inside of the body, and the first and the second flanges 30 and 31 are connected to each other with a flexible port 32 and are attached in such a manner that both flanges 30 and 31 sandwich the abdominal wall 12. The flexible port 32 is formed of, for example, a silicone rubber or the like. When the flexible port 32 is attached on the abdominal wall 12, the flange 31 on the side inside of the body is deformed to be inserted from the sectioned part 15. The second valve 2 is located inside of the flexible port (communication body) 32 while the first valve 1 is provided on the end part of the bellows 29 which are connected to the flange 30 on the side outside of the body.

By connecting the first valve 1 and the flexible port 32 to the bellows 29, there is an advantage in that the insertion of the hand into the access device can be carried out with one hand without leaking gas at all, and, in addition, after the insertion of the hand, the bellows 29 can be easily deformed so that an approach of the hand into the abdominal cavity can be made in different directions (refer to an arrow and broken lines in FIG. 12).

Figure 13:
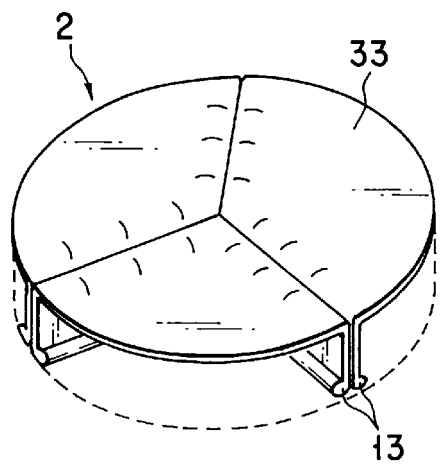
FIG. 13 is a perspective view showing a first modification of the second valve.
Figure 14A:
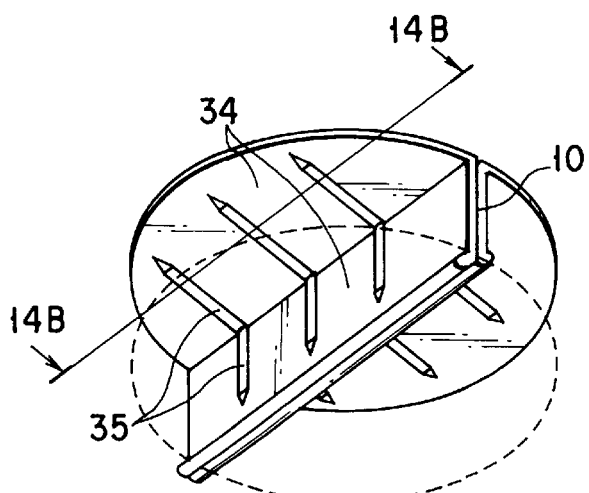
FIG. 14A is a perspective view showing a second modification of the second valve.
Figure 14B:
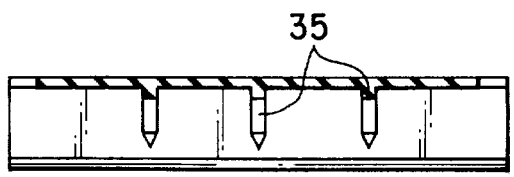
FIG. 14B is a sectional view taken along line 14A–14B of FIG. 14A.

FIG. 13 shows a different example of the second valve 2. In this manner, even a three-fan-shaped valve 33 serves for the air-tight function as the second valve 2. In such a case, there is an advantage in that since the open part is larger than the second valve 2 according to the first embodiment in the state in which the second valve 2 is open, the insertion resistance of the hand becomes smaller. However, it is necessary to form a state in which the valve is approximately closed by providing a rigidity on the folded back end part 13. Furthermore, with respect to the second valve 2 of the type shown in FIGS. 14A and 14B, a plurality of ribs 35 is provided on a thin film which forms the second valve 2, and on a rear surface 34 of a contact surface 10 in a vertical direction with respect to a slit-like open part 8. As a consequence, when the hand is inserted into or removed from the second valve 2, the ribs 35 prevent the valve from not returning to a natural state (the state in which the valve is approximately closed) by means of the revere of the contact surface 10 so that more secure air-tight state can be obtained.

Figure 15A:
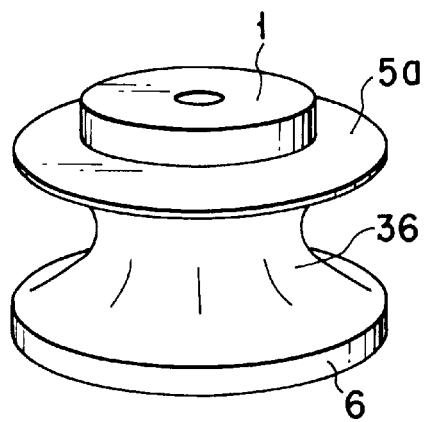
FIG. 15A is a perspective view of the access device for the surgical treatment according to a fourth embodiment of the invention.
Figure 15B:
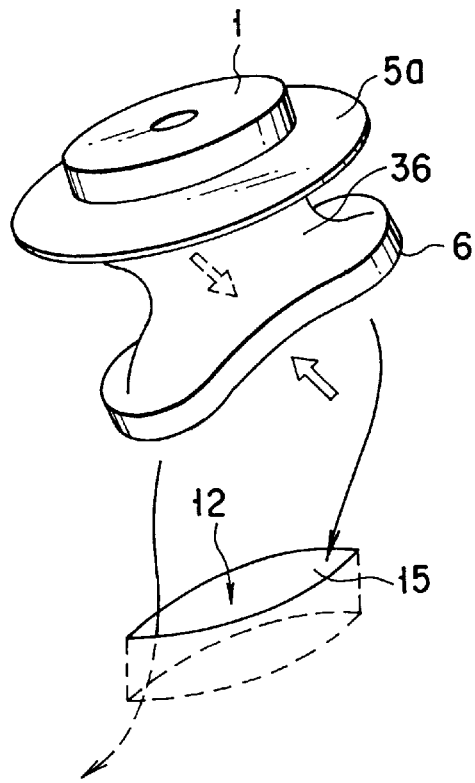
FIG. 15B is a perspective view showing a state in which the access device of FIG. 15A is modified for being attached on the abdominal wall.

FIGS. 15A and 15B show a fourth embodiment of the present invention. Only points which are different from the points in the first embodiment will be explained hereinbelow. The flange part 5a and the removal prevention ring 6 are connected to each other with an expandable sleeve (communication body) 36. The distance between the flange part 5a and the removal prevention ring 6 is arbitrarily set with the expandable sleeve 36. The flange part 5a and the removal prevention sleeve 6 are inserted into the abdominal cavity from the sectioned part 15 by deforming the half-solid removal prevention ring 6 as shown in FIG. 15B. This work can be easily performed because the expandable sleeve 36 is expanded freely. After the removal prevention ring 6 is inserted, the elastic force of the expandable sleeve 36 works in such a manner that the abdominal wall 12 is sandwiched with certitude between the flange part 5a and the removal prevention ring 6 and the flange part 5a and the removal prevention ring 6 are fixed there.

Figure 16:
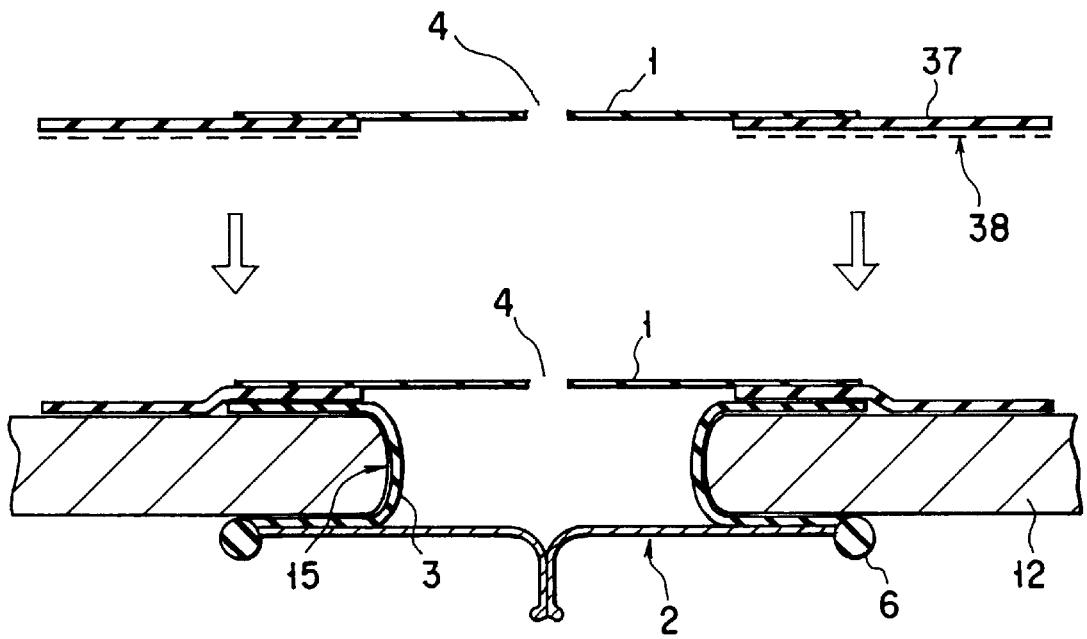
FIG. 16 is a sectional view of the access device for the surgical treatment according to a fifth embodiment of the invention.

FIG. 16 shows a fifth embodiment of the present invention. Only points which are different from the points in the first embodiment will be explained hereinbelow. The first valve 1 comprises a circular elastic thin film having a hole 4 for allowing the hand to be inserted thereinto, and the first valve 1 is stuck on an upper surface of a disc-shaped sealing film 37. The rear surface of the sealing film 37 forms a sticking surface 38. The second valve 2 is located on the same surface as a circular surface which forms a removal prevention ring 6 having an appropriate hardness, and the second valve 2 is integrally connected to the sleeve 3 which is expanded from an outside surface of the removal prevention ring 6.

After the removal prevention ring 6 is deformed and the second valve 2 is arranged in the abdominal cavity in the same manner as the first embodiment, the sleeve 3 on the side outside of the body is stuck to be covered with the sticking surface 38 of the sealing film 37. At this time, gas leakage from a slit between the sleeve 3 and the sectioned part 15 can be completely prevented with the sealing film 37 with the result that it is not required that the removal prevention ring 6 is always allowed to adhere to the abdominal wall 12.

In this structure, since the sleeve 3 itself becomes compact so that the sleeve 3 is hardly projected to the outside of the body after the attachment thereof, the sleeve 3 does not cause a trouble to the work. Furthermore, in the case where the attachment position is not plane and a curved surface is formed with the pneumoperitoneum, the sleeve 3 can be sealed along a curvature of the abdominal wall 12.

Figure 17:
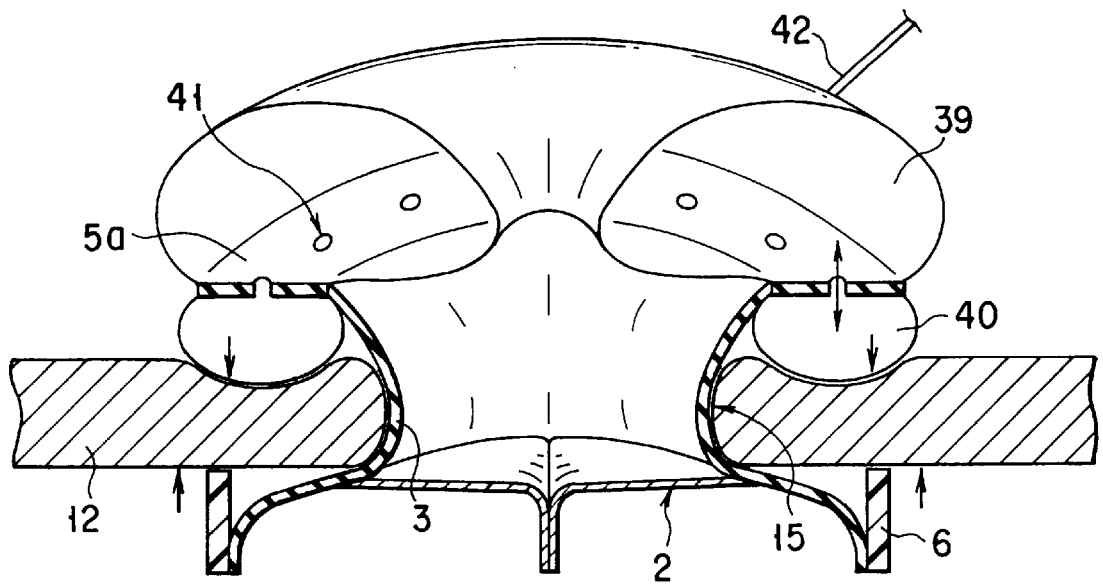
FIG. 17 is a perspective view showing a state in which the access device for the surgical treatment according to a sixth embodiment of the invention is attached on the abdominal wall, the view being accompanied by a cross section of the access device.
Figure 18:
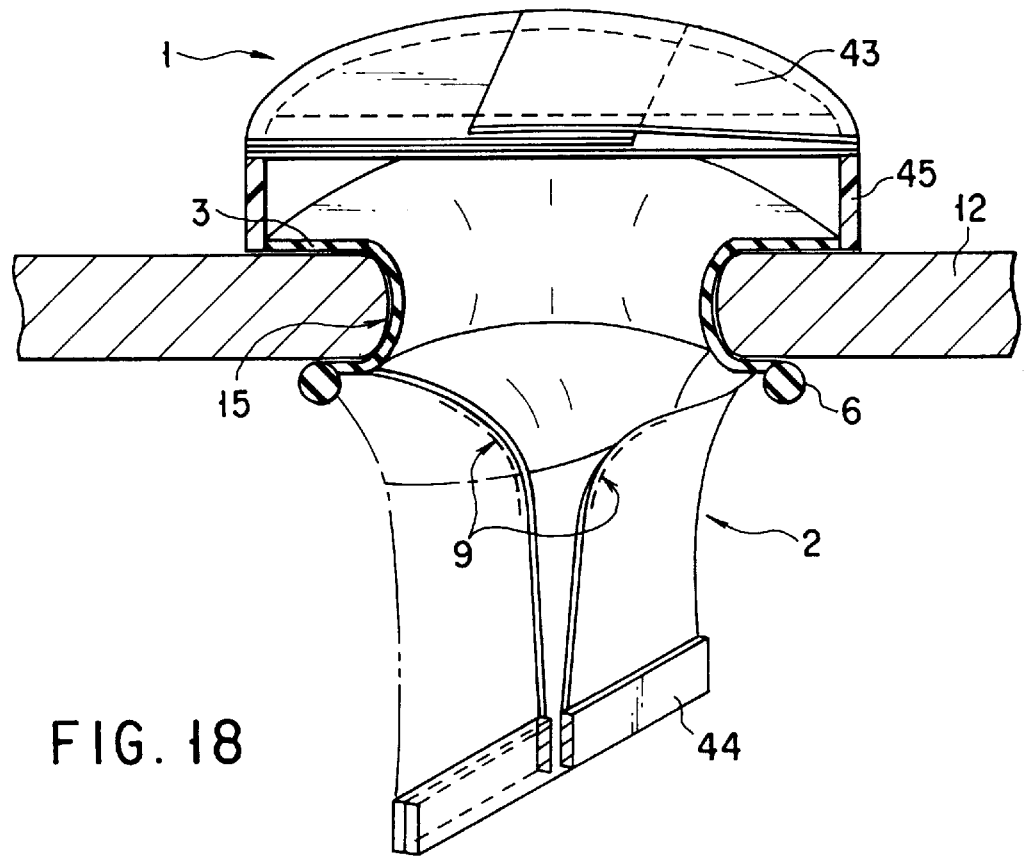
FIG. 18 is a perspective view showing a state in which the access device for the surgical treatment according to a seventh embodiment of the invention is attached on the abdominal wall, the view being accompanied by a cross section of the access device.

FIG. 17 shows a sixth embodiment of the present invention. Only points which are different from the points in the first embodiment will be explained hereinbelow. On the upper surface and the lower surface of the flange part 5a on the side outside of the body, a donut-like swollen member is arranged which member is swollen with a fluid which is injected with an injection route 42. The inside diameter of the swollen member 39 on the upper surface of the flange part 5a is thinner than the wrist of the surgeon, and functions as the first valve 1. In other words, in the state in which the hand is inserted, the swollen member 39 adheres to the circumference of the hand or an arm to secure the air-tight state. Furthermore, after the access device is set on the sectioned part 15, the swelling member 40 on the lower surface of the flange part 5a is swollen so that the abdominal wall 12 is sandwiched with the removal prevention ring 6 and the swollen member 40 thereby being fixed to the sectioned part 15 with certitude and, at the same time, serving to prevent the gas leakage between the sectioned part 15 and the sleeve 3.

On the flange part 5a, a plurality of holes 41 are provided which connect the inside of the swollen member 39 to the inside of the swollen member 40 with the result that the fluid inside of the swollen members 39 and 40 can be moved through the holes 41. Generally in the case where the hand inserted into the cavity of the body is largely moved, the gas is liable to be leaked particularly from a slit between the sleeve 3 and the sectioned part 15. However, in this structure, pressures inside of the swollen members 39 and 40 which follow the movement of the hand are well balanced to function in such a manner the slit is not opened thereby making it possible to seal this part completely.

FIGS. 18 through 20A and 20B show a seventh embodiment of the present invention. Only points which are different from the points in the first embodiment will be explained hereinbelow. In the same manner as the first embodiment, with the access device according to the seventh embodiment, the sleeve 3 protects the sectioned part 15, a removal prevention ring 6 is arranged inside of the body, and a ring-like member (ring 45 outside of the body) is arranged outside of the body with the result that the abdominal wall 12 is sandwiched with the removal prevention ring 6 and the ring-like member (ring 45 on the side outside of the body) and the removal prevention ring 6 and the ring-like member are fixed there.

Figure 19:
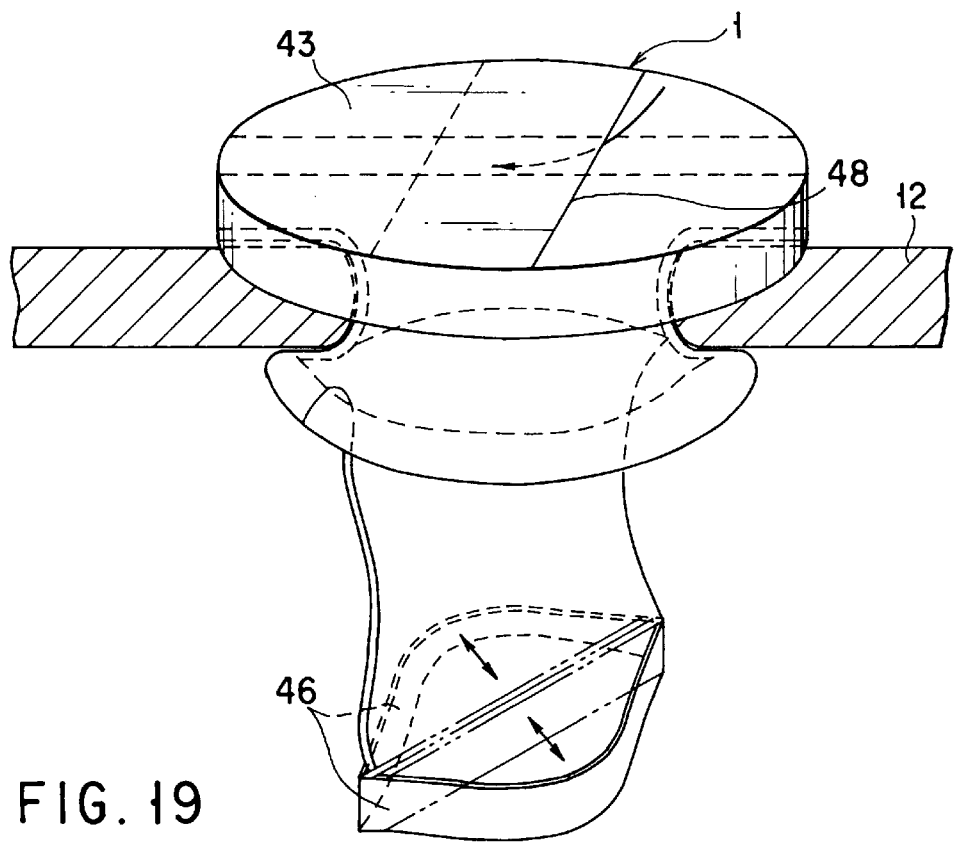
FIG. 19 is a perspective view showing one operation state of the access device shown in FIG. 18.
Figures 20A, 20B:
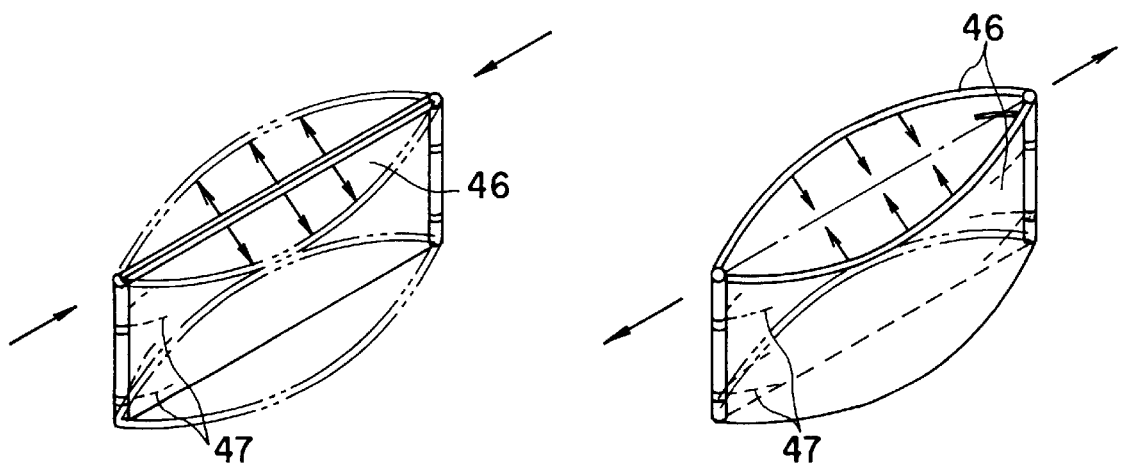
FIG. 20A is a perspective view showing a state in which a second valve according to the modification of the access device shown in FIG. 18 is closed.
FIG. 20B is a perspective view showing a state in which the second valve according to the modification of the access device shown in FIG. 18 is open.

The first valve 1 is arranged in such a manner that a plurality of semi-circular thin films 43 are overlapped with each other at the central part thereof and the first valve 1 seals the circumference of the arm in the state in which the hand is inserted. The second valve 2 comprises a thin film which is extended from the inside surface of the removal prevention ring 6 and a contact surface which is formed with closing means 44 which is provided on the end part of the thin film. As shown in FIG. 19, the closing means 44 may be such that, for example, a pair of flexible magnets are arranged on an end part of the second valve 2. The closing means 44 may also be formed of plate springs 46 and 46 having a spring characteristic as shown in FIGS. 20A and 20B, and a twisted spring 47 provided on both sides thereof in order to energize a pair of plate members 46 and 46 in a direction that the plate springs 46 and 46 are closed. In the former case, there is an advantage in that since the closing means is formed of magnet, the magnetic force becomes small to such an extent that the magnetic force can be ignored once the closing means is opened with the result that a force received from the closing means is virtually zero in the state in which the hand is inserted.

When the hand is inserted, the hand is inserted by groping for the open part of the next thin film from the open part 48 of the semi-circular thin film 43 located at an outermost position of the first valve 1 (Refer to an arrow shown in FIG. 19). Since this thin film is very thin and forms a plurality of layers, the film serves as a valve in a sufficient manner, and, in addition, a force fastening the arm is very small.

Furthermore, in this structure, the pressure (pneumoperitoneum pressure) is received from the abdominal wall side of the second valve 2. As a consequence, the force is received not only on the part of the closing means 44 but also on an overall part of the thin film of the second valve 2 in such a manner that the inside surface of the thin film adheres to each other thereby making it possible to secure the air-tight state thereof.

Next, a usage state of the access device for surgical treatment is shown. The length of the sectioning for the access device is set to a minimum required length (of about 5 to 7 cm) which enables the insertion of the hand up to the elbow of the surgeon. The sectioned part is located in the lower abdominal part (bythus). There is an advantage in that the sectioning can be much smaller than in the normal peritoneotomy in which the center of the abdomen is sectioned to a length of about 15 to 25 cm and, and the pain is smaller and the operation is more excellent in terms of esthetic point of view because the bythus is sectioned.

As described in the first embodiment, the sectioned part is expanded with an unguiculus and part of the removal prevention ring 6 is inserted into the abdominal cavity and the access device of the embodiment is fixed to the abdominal wall 12 with the sleeve fixing member 5 and the removal prevention ring 6 (the access device is fixed in such a manner that the sectioning direction and the slit direction of the second valve 2 agree with each other). An appropriate method is adopted for each of the embodiments for fixing the access device to the abdominal wall 12.

In the same manner as the normal operation under celioscope, the pneumoperitoneum operation is performed, and a required number of trocars are penetrated while an image in the scope is confirmed on the monitor. Since the trocars can be penetrated while the abdominal wall is supported from the side of the abdominal cavity with the hand so that organs in the abdominal wall is not damaged with the blade of the trocars at this time, the operation is very safe. When the operation is performed with one hand being inserted into the abdominal cavity, the left hand is inserted therein and the forceps having a long shaft is manipulated with the right hand. The following operations are performed with the left hand; (1) confirmation of the anatomy of the organs, (2) improvement of field of vision and exclusion of the organs for securing the field of operation, (3) confirmation and grasp of the circulation through the touch of palpation of beats, (4) obtuse ablation of agglutinated part, (5) treatment of bleeding (gauze is inserted to apply an angiopressure), and the like. Thus, the left hand can perform functions which cannot be done with the conventional forceps having a long shaft. As a consequence, much information can be obtained with the result that a swift treatment can be administered. Such information can be obtained and such treatment can be easily administered by the surgeon in the celiotomy. However, such information cannot be obtained and such treatment cannot be administered in the conventional operation under endoscope. It is considered that this point is a factor which makes the operation under the endoscope difficult and prolongs the OPE time. Consequently, in the operation according to the invention, the difficult operation which takes a lot of time under the conventional endoscope is enabled (the treatment can be administered in a short time because the closure and banding can be performed with the same sense as, for example, the celiotomy, and the development of the tissue and the involvement of the tissue on the rear side can be confirmed when the tissue is closed with an automatic closure machine).

Figure 21:
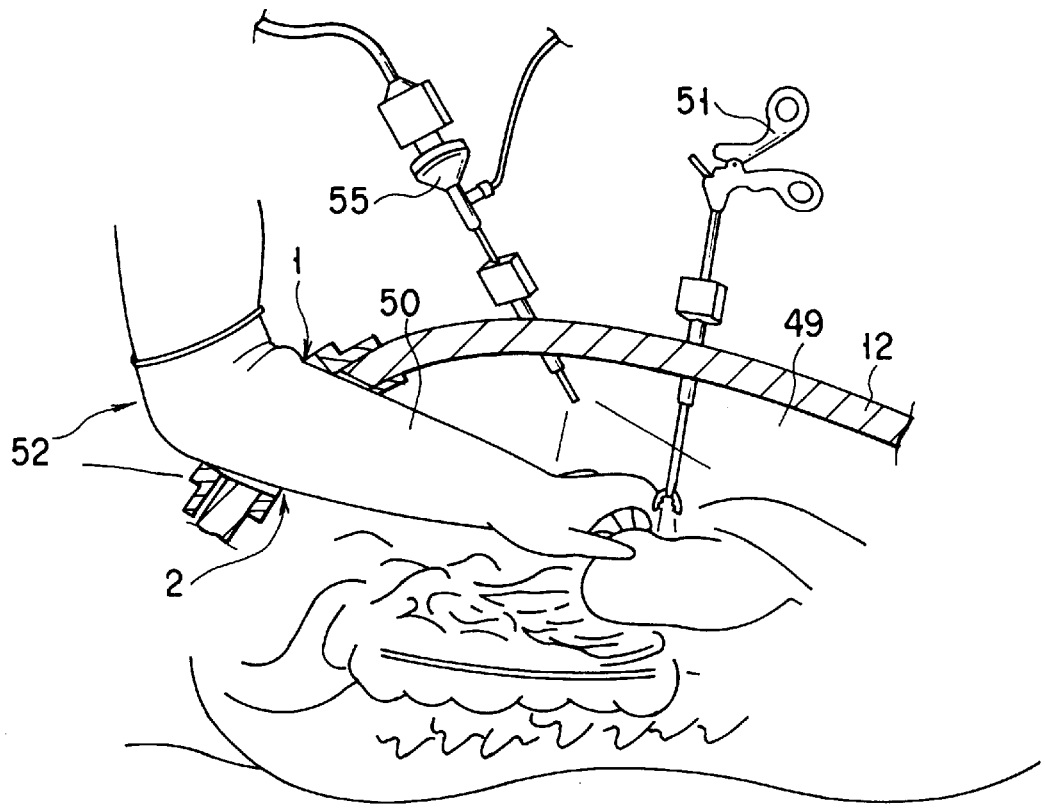
FIG. 21 is a perspective view showing one form of a usage of the access device for the surgical treatment of the invention.

FIG. 21 shows a state in which the operation of the invention is performed. Since the abdominal cavity has a sufficient space 49 for treatment, the treatment can be administered with a cooperative operation with the forceps 51 having a long shaft in the state in which the left hand 50 is inserted approximately to the elbow. At this time, gas in the abdominal cavity is held with the first valve 1, and the air-tight state can be held against various movement of the hand. Furthermore, in the case where the treatment is administered only with the forceps 51 having a long shaft, the air-tight state is held by the second valve 2 with the result that the treatment can be administered in a situation completely similar to the situation of the normal operation under the endoscope. Incidentally, it is required that the gloves 52 used by the surgeon are a long type which covered the arm up to the elbow.

Figure 22:
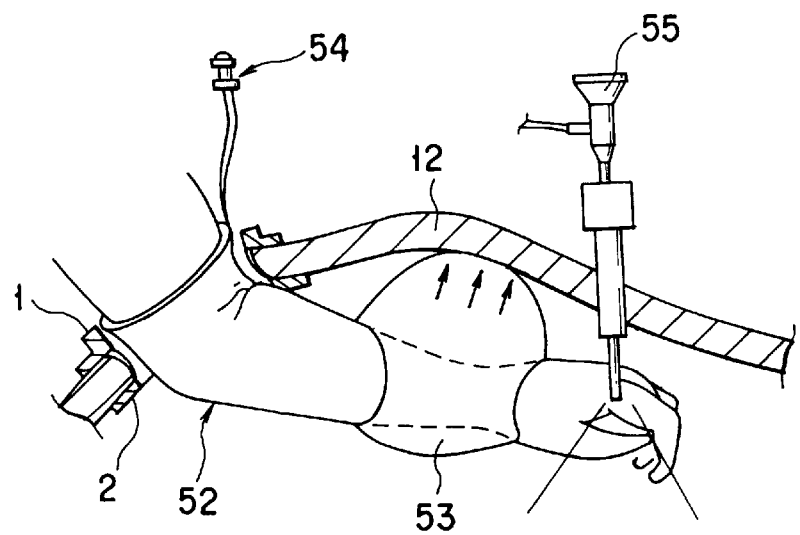
FIG. 22 is a perspective view showing a first form of a usage of the access device for the surgical treatment of the invention.

FIG. 22 shows an example in which a swelling member 53 (balloon) is provided on the part of the wrist of the aforementioned gloves 52 to actively provide a treatment space.

As is generally known, when the pressure in the abdominal cavity 12 is too high, the complication such as an influence against the respiratory system, a damage to the diaphragm, and an influence against the circulation behavior is generated. Consequently, it is desired that the pressure therein is set to a lower level. On the other hand, it is favorable that the pressure is high in terms of the confirmation of the cavity to be treated. In order to solve this problem, the balloon 53 is attached on the part of the wrist to push up actively the abdominal wall 12 in the vicinity of the portion to be treated by injecting a fluid from an injection port 54 which is introduced to the outside of the body and swelling the balloon 53 (refer to an arrow in FIG. 22). Since the wrist is fastened with the balloon at this time, it is favorable that the part of the wrist is protected with a hard pipe or the like to prevent the force from being applied thereon. Incidentally, it is favorable that the swelling direction may be changed depending upon the usage by enlarging the dorsum of the hand and diminishing the palm.

Next, another usage example will be explained.

As has been already described, there are provided many advantages as compared with the conventional surgical operation under the endoscope. It is more desirable that the operation is performed in a form more approximate to the celiotomy in a more fine work. For example, it is more effective to carry out a closure operation by holding a needle head in the right hand and holding a pincers in such operations as the end-to-end anastomosis of the intestine or the like. Then the surgeon can perform the anastomosis operation with the same sense as the celiotomy by inserting both hands into the abdominal cavity. In this case, a sectioned part having a required length is provided in the right and the left lower bythus, and the access device is installed there. Only the left hand is inserted when needed, and the part is treated with the right hand by using the forceps having a long shaft (in the case where the left hand is not removed during the operation, the access device for the left hand may not require the valve 2).

When both hands are inserted, it becomes necessary that a treatment tool such as forceps or the like is introduced into the abdominal cavity to administer the treatment similar to the celiotomy. However, since there is no wide space which allows the insertion of the treatment tool for operation as it is into the abdominal cavity, a small-size dedicated treatment tool is required. Furthermore, it is necessary to think out a device such as, for example, an attachment of a wire at the end of the forceps for recycling the forceps with certitude because a plurality of forceps are introduced into the abdominal cavity. Furthermore, in the treatment tool having an electrotome and cords such a water supply and absorption tube or the like, a supply line for the purpose will be needed.

Figure 23:
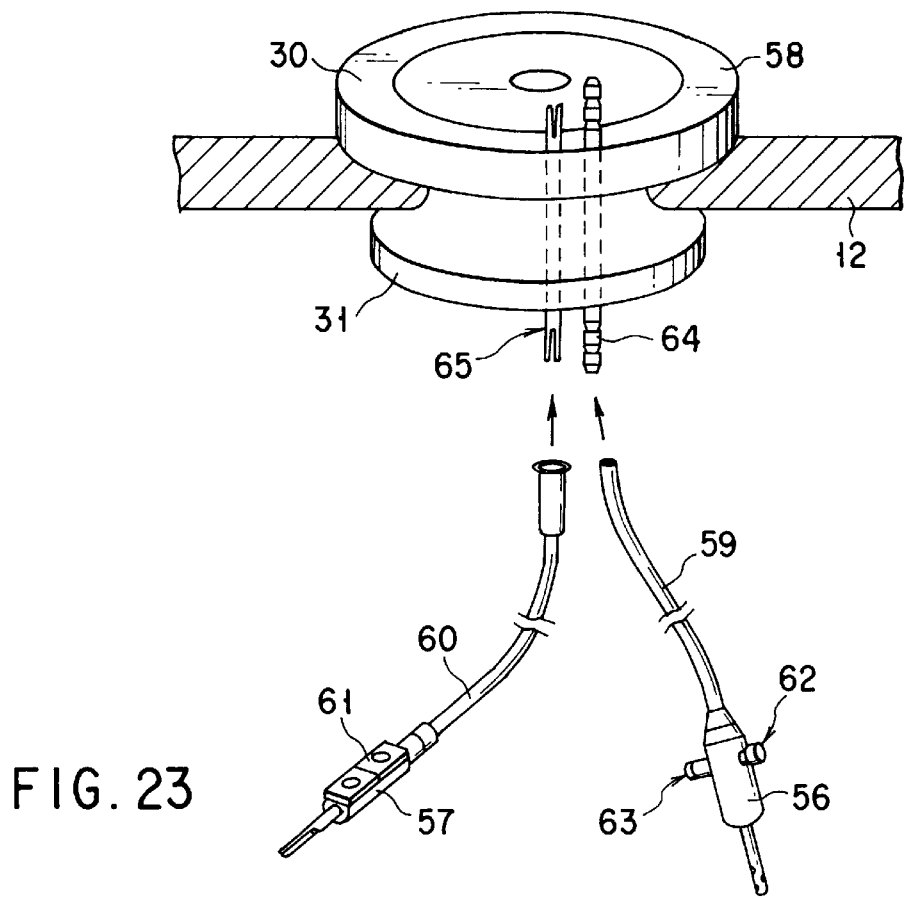
FIG. 23 is a perspective view of the access device having a connection part of a treatment tool.

FIG. 23 shows an example of the water supply and absorption tube (the suction and irrigation tube) 56, the electrotome 57 which can be handled in the abdominal cavity and the access device 58 having connection parts of the cords (tubes) 59 and 60 for the tube 56 and the electrotome 57.

The operation part of the water supply and absorption tube 56 is very small with a size which can be held by the hand, and water can be supplied and absorbed from the end part by pressing the water supply button 62 and the water absorption button 63 provided on the main body part (side holes are provided for the prevention of the blockage on the outside surface of the tube at the end part). The tube 59 is set to a length of about 20 through 30 cm so that the tube 59 can be easily handled in the abdominal cavity. On the inside thereof, a double lumen is formed wherein the water supply/absorption tube 59 is independent. On the other hand, the electrotome has a size which can be held in the hand in the same manner as the water supply and absorption tube 56. The electrotome has a shorter cord 60 for supplying a high frequency current and is capable of allowing the flow of high frequency current for coagulation and section with a hand switch 61 provided on an operation part.

The tube 59 and the cord 60 are connected to the outside of the body, and the line comprises a connection part which is provided so as to be projected toward a flange 30 of the access device 58 on the side outside of the body and a flange 31 thereof on the side inside of the body (a mouthpiece for tube connection 64, and a cord connection pin 65).

Figure 24A:
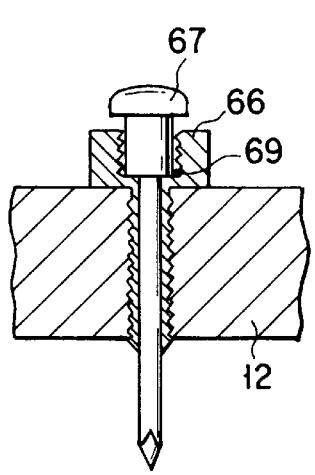
FIG. 24A is a sectional view showing one form of the usage of the access device having the connection part of the treatment tool.
Figure 24B:
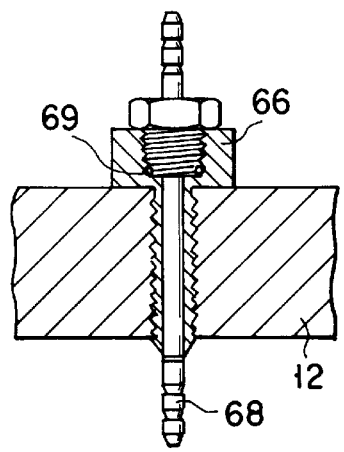
FIG. 24B is a sectional view showing a second form of the usage of the access device having the connection part of the treatment tool.
Figure 24C:
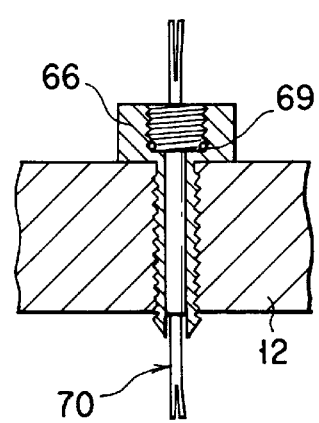
FIG. 24C is a sectional view showing a third form of the usage of the access device having the connection part of the treatment tool.

FIG. 24A through 24C show a dedicated device of the treatment tools having the aforementioned cord, the device connecting the outside of the body and the inside thereof. The dedicated device is very thin (with, for example, an outside diameter of 2 to 3 mm), and comprises an abdominal wall fixture 66, an inside needle 67 which is inserted into the inside of the fixture 66, a tube connection member 68, and a cord connection member 70. FIG. 24A shows a state in which the dedicated device is penetrated into the abdominal wall 12. On the outside surface of the abdominal wall fixture 66 which surface contacts the abdominal wall 12, a screw part is provided which is rotated with respect to the abdominal wall 12 to be inserted and fixed thereto. Furthermore, on the inside surface of the abdominal wall fixture 66 at the side of the hand, a screw is provided. On the bottom part thereof, an O-ring 69 is arranged. When the O-ring 69 and the inside needle 67 are assembled, the gas leakage is prevented. When the water supply and absorption tube 56 is used, the inside needle 67 is removed therefrom, and the tube connection member 68 is inserted thereinto in place of the inside needle 67 as shown in FIG. 24B. At the hand side of the tube connection member 68, there is provided a screw which is engaged with the screw of the abdominal wall fixture 66, and the tube connection member 68 is installed in the air-tight manner by fastening the screw thereof. In the case where the electrotome is used in the same manner, the cord connection member 70 may be attached instead as shown in FIG. 24C. With such a procedure, there is an advantage in that since the supply line may be installed only with a very small hole, the supply line can be installed at a desired position of the surgeon, and the treatment in the abdominal cavity can be effectively administered.

Figure 25:
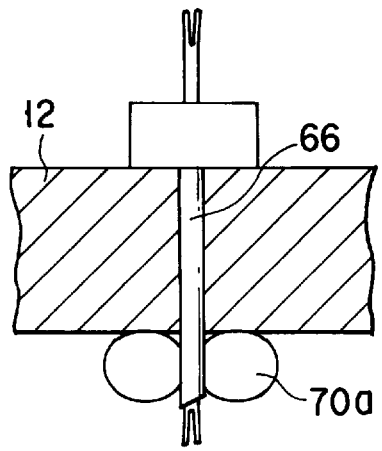
FIG. 25 is a sectional view showing a state in which the treatment tool is fixed to the abdominal wall.

Incidentally, the abdominal wall fixture 66 may be fixed to the abdominal wall 12 by providing a balloon 70a which is swollen in a donut-like shape on an outside surface at the end side which surface is fixed to the abdominal wall as shown in FIG. 25.

Figure 26A:
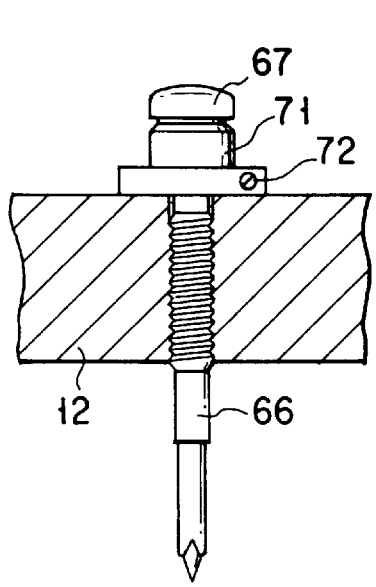
FIG. 26A is a sectional view showing a first usage form of an abdominal wall fixture fixed to the abdominal wall.
Figure 26B:
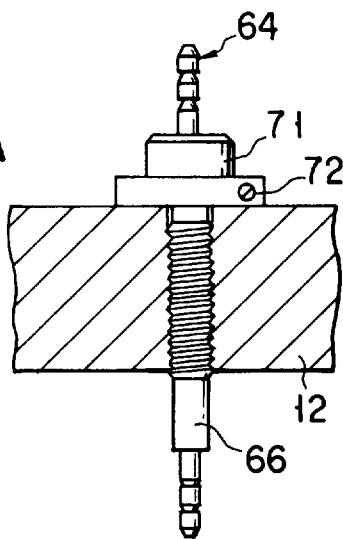
FIG. 26B is a sectional wall showing a second usage form of the abdominal wall fixture fixed to the abdominal wall.
Figure 26C:
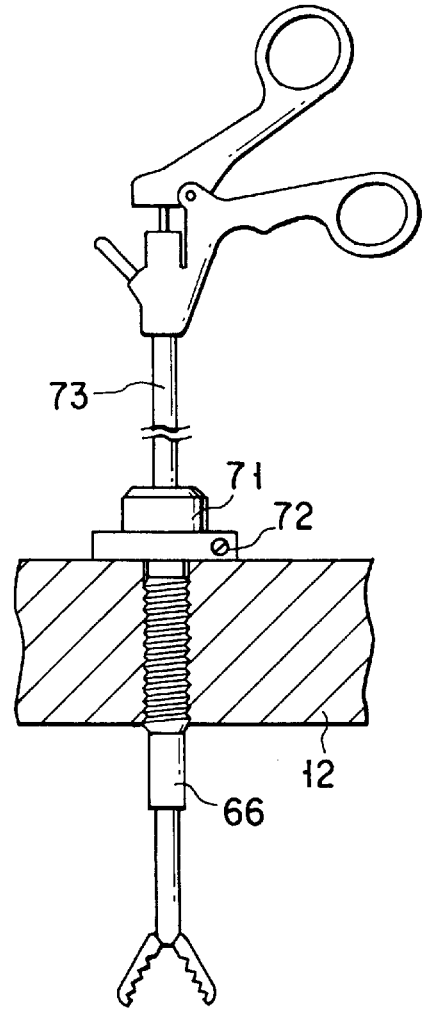
FIG. 26C is a sectional wall showing a third usage form of the abdominal wall fixture fixed to the abdominal wall.
Figure 27:
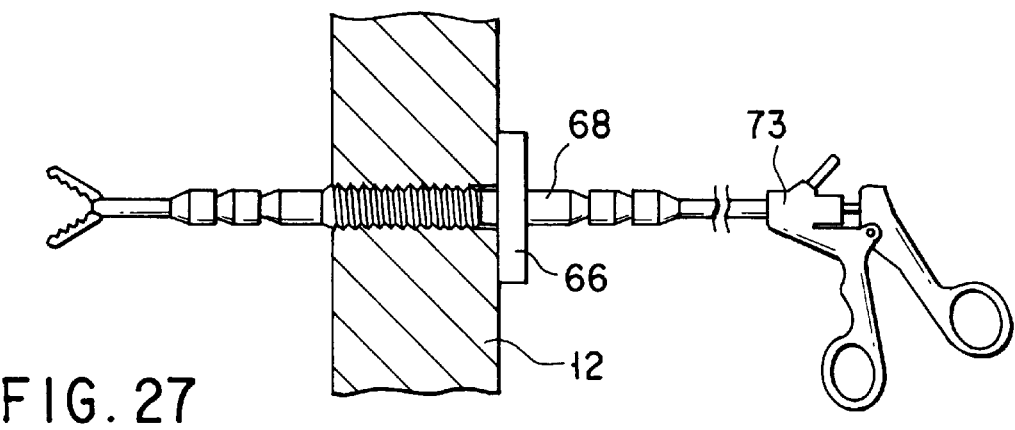
FIG. 27 is a sectional wall showing a fourth usage form of the abdominal wall fixture fixed to the abdominal wall.
Figure 28A:
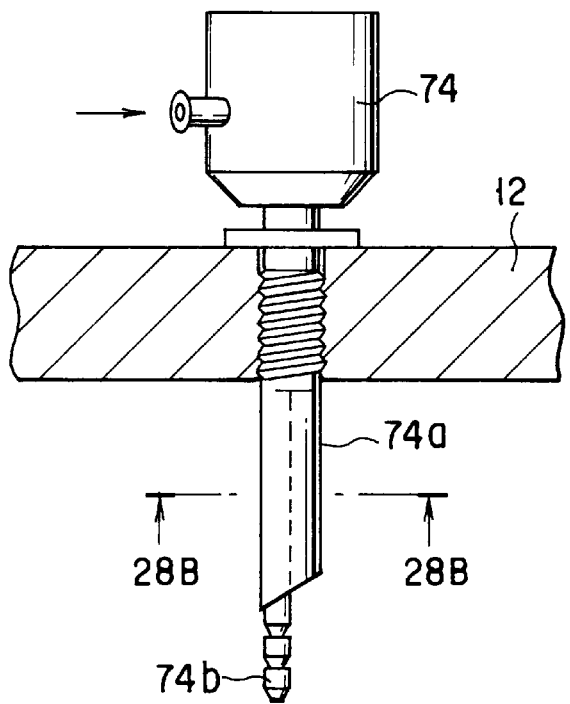
FIG. 28A is a sectional wall showing a fifth usage form of the abdominal wall fixture fixed to the abdominal wall.
Figure 28B:
FIG. 28B is a sectional view taken along line 28A—28B of FIG. 28A.

FIG. 26A through 28B show other examples. As shown in FIG. 26A, the abdominal wall fixture 66 and the inside needle 67 are fixed with the fastening screw 72 so that the air-tight state is held with a rubber cap 71. As shown in FIG. 26B, the tube connection mouthpiece 64 is inserted into the inside of the abdominal wall fixture 66 and is fixed with the fastening screw 72 so that it becomes possible that the water supply and absorption tube 56 is used in the abdominal wall 12. Furthermore, as shown in FIG. 26C, the forceps 73 having the long shaft can be inserted and can serve as a so-called trocar. In addition, as shown in FIG. 27, the abdominal wall fixture 66 itself which allows the insertion of the forceps 73 having the long shaft may serve as the tube connection member 68. Otherwise, as shown in FIG. 28, a tube 74b is provided independent of a tube 74a for inserting the forceps having the long shaft of the surgical instrument 74 so that the tube 74b may be used for the tube connection.

Figure 29:
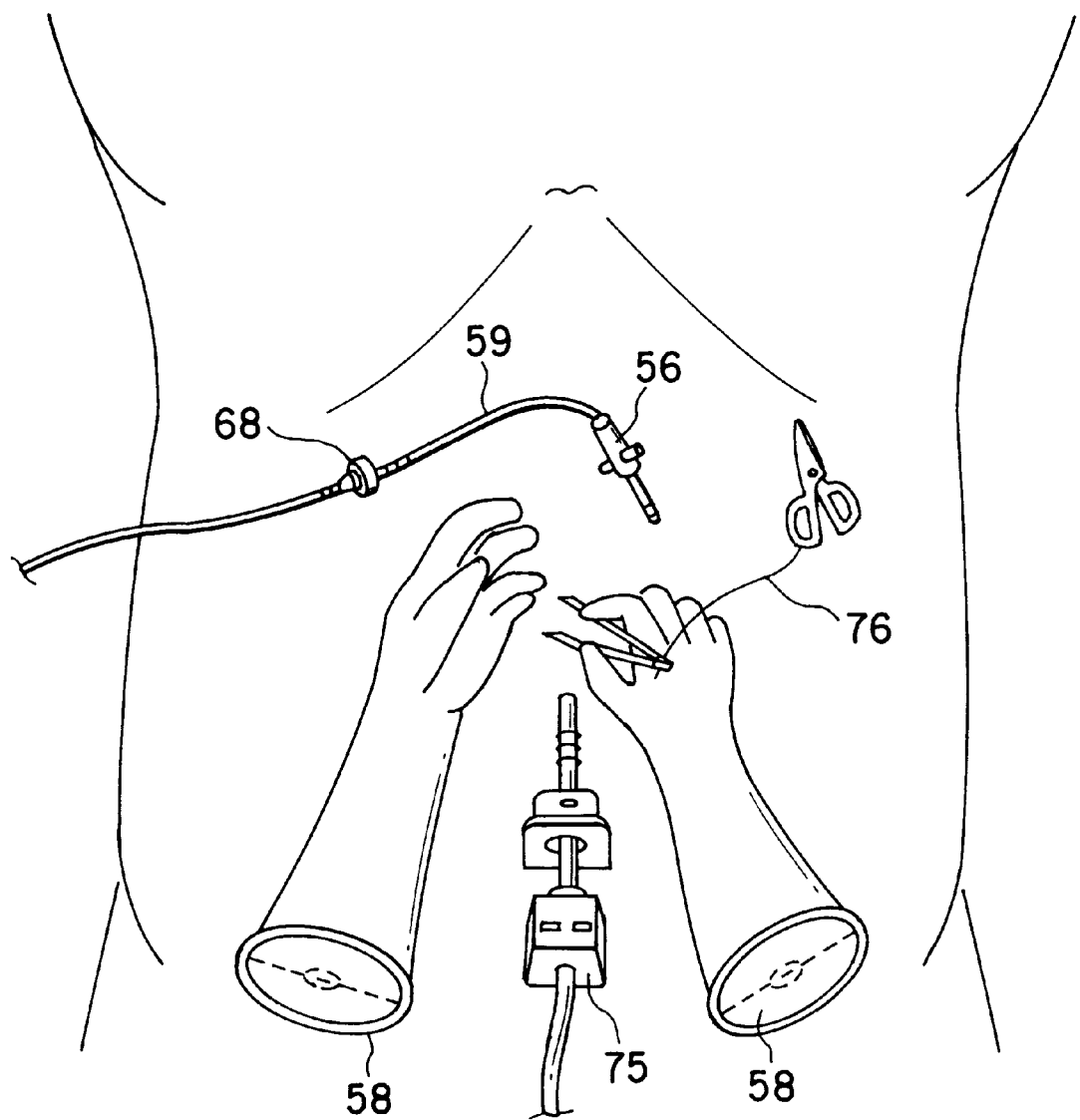
FIG. 29 is a perspective view showing a state in which a treatment is administered by inserting both hands into the abdominal cavity.

FIG. 29 shows a state in which both hands are inserted into the abdominal cavity for treatment. Both hands are inserted from the lower abdomen on both sides of the patient and the treatment is administered under observation with the scope by using small-size pincers and iron forceps which are inserted from the access device in advance (these forceps are connected with the wire for securing the recycling from the inside of the abdomen). The water supply and absorption tube 56 is inserted when needed so that the access device can be connected with the outside of the body by connecting the tube connection member 68 and the tube 59. Furthermore, though not shown, the electrotome may be introduced into the abdominal cavity for treatment. Such treatment is appropriate for fine work in which closure, banding and delicacy are required with the result that the treatment corresponding to the celiotomy can be administered.

Furthermore, as an application example of a treatment tool for administering the treatment in the abdominal cavity, FIGS. 30A through 31B can be considered. In other words, the function of the treatment tool having a cord and the cord thereof are integrally provided in dedicated long gloves which are used in combination with the access device. FIG. 30A shows a state in which the function is provided on the finger tip of dedicated gloves 77. On the abdominal side of the index finger and the abdominal side of the thumb, electrodes A78 and B79 are provided so that the tissue can be sandwiched therebetween thereby enabling coagulation and hemostasis by allowing the high frequency current to flow (at this time, a bi-polar electrode may be formed with the electrode A78 and the electrode A79).

Figure 31A:
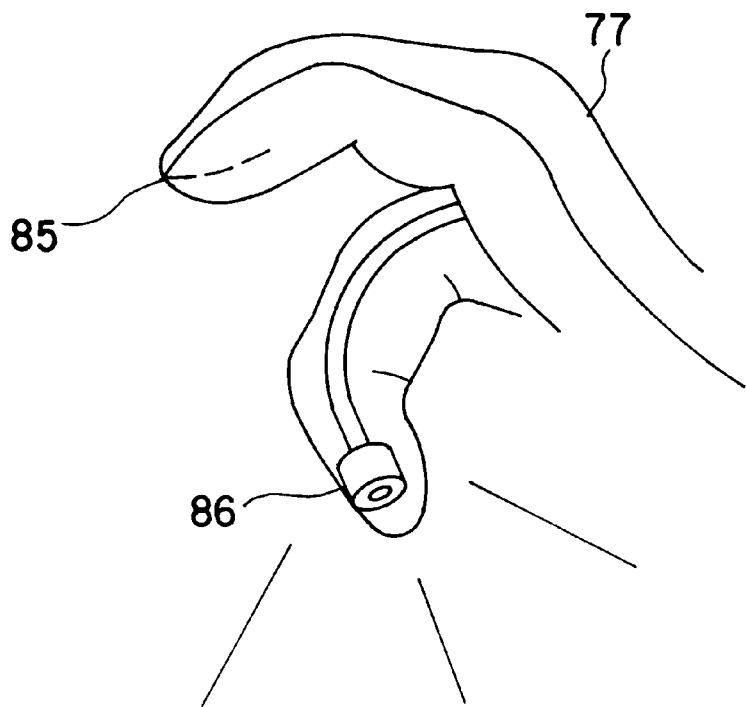
FIG. 31A is a perspective view showing a state in which an electrode and a CCD camera is attached on a finger tip of dedicated gloves for administering the treatment in the abdominal wall.
Figure 31B:
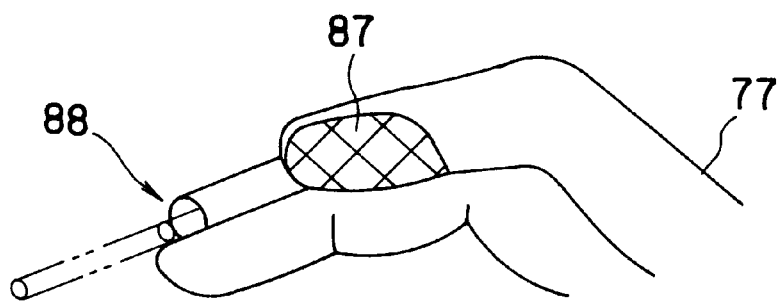
FIG. 31B is a perspective view showing a state in which a gauze or a localized syringe needle is attached on a finger tip of a dedicated gloves for treating the abdominal cavity.

Furthermore, on the nail side of the index finger, a water supply and absorption port (a suction and irrigation port) 81 is arranged. The cords 80 and 82 are integrally formed with the dedicated gloves 77 as shown in FIG. 30B and FIG. 30C thereby preventing the generation of the gas leakage because the cords 80 and 82 are introduced to the side of the first valve 1 and the second valve 2 of the access device on the side outside of the body. The cords 80 and 82 are bundled with the connector A83 and is connected with one touch to the cord B84 which bundles the cords 80 and 82 on the side of the main body. In addition, as shown in FIGS. 31A and 31B, various forms (which can be freely projected and recessed) can be considered such as a type which is provided with an electrode 85, a CCD camera 86, a gauze 87 (a device similar to a swab which is used for the obtuse ablation of the tissue of the living body), a catheter, a localized syringe needle 88, a laser probe or the like (the form can project or depress as the like). In addition, gloves provided with a light guide can be considered.

Figure 32:
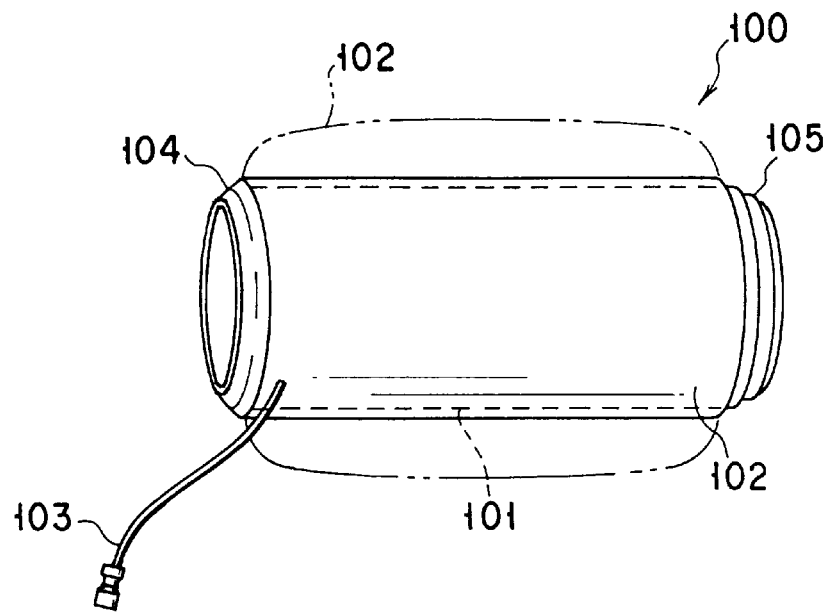
FIG. 32 is a perspective view of a sleeve which is used together with the access device.

FIG. 32 shows a sleeve 100 which is used together with an access device 90 (refer to FIG. 33) which is substantially the same with the access device according to the first embodiment of the invention. This sleeve 100 is attached on the arm of the surgeon. The sleeve 100 has a solid or a half-solid tube-like main body 101 having an inside diameter through which the arm of the surgeon can be penetrated, and a thin film 102 which is covered with the outside circumference of the main body and which can be swollen. In this case, only both end parts of the thin film 102 can be air-tightly fixed to the main body of the device. Furthermore, to the thin film 102, a tube 103 is connected to allow the injection of a fluid into a space between the thin film 102 and the main body 101. When fluid is injected into the space between the thin film 102 and the main body 101 through the tube 10, the thin film 102 is swollen as shown by a two dot chain line shown in FIG. 33. Incidentally, on both end parts of the main body 101, expandable sealing members 104 and 105 are provided.

Figure 33:
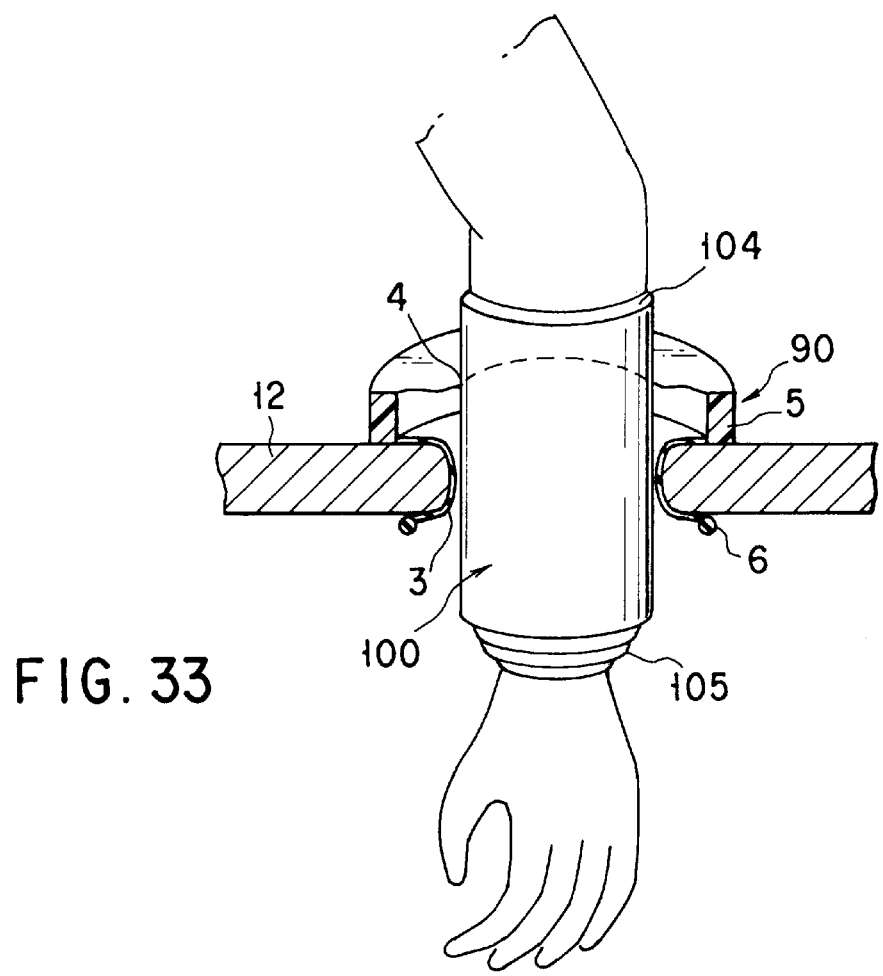
FIG. 33 is a sectional view showing a state in which an arm on which the sleeve is attached is inserted into the inside of the body through the access device.

FIG. 33 shows a state in which the arm attached with the sleeve 100 is introduced into the inside of the body through the access device 90. In this manner, in the state in which the sleeve 100 is attached on the arm, the sealing member 104 and 105 provided on both sides of the main body 101 are located in the vicinity of the wrist and the elbow respectively and adhere to each other. In addition, the thickness of the arm which is introduced into the inside of the body through the access device 90 is held on an even level over the whole length because the arm is inserted into the inside of the tube-like main body 101. Consequently, it is not necessary to set the material quality, the form, the thickness or the like of the first valve 4 in accordance with a thick part and a thin part of the arm unlike each of the aforementioned embodiment. In other words, the material quality, the form, the thickness and the like of the first valve 4 may be set only in accordance with the outside diameter of the main body 101. Furthermore, the fastening force with the first valve 4 and the second valve 2 (not shown) does not work on the arm which is inserted into the main body 101. Incidentally, since the sealing members 104 and 105 are provided to secure the sealing characteristic around the arm, the sealing members 104 and 105 may be provided on one side of the main body 101.

Figure 34:
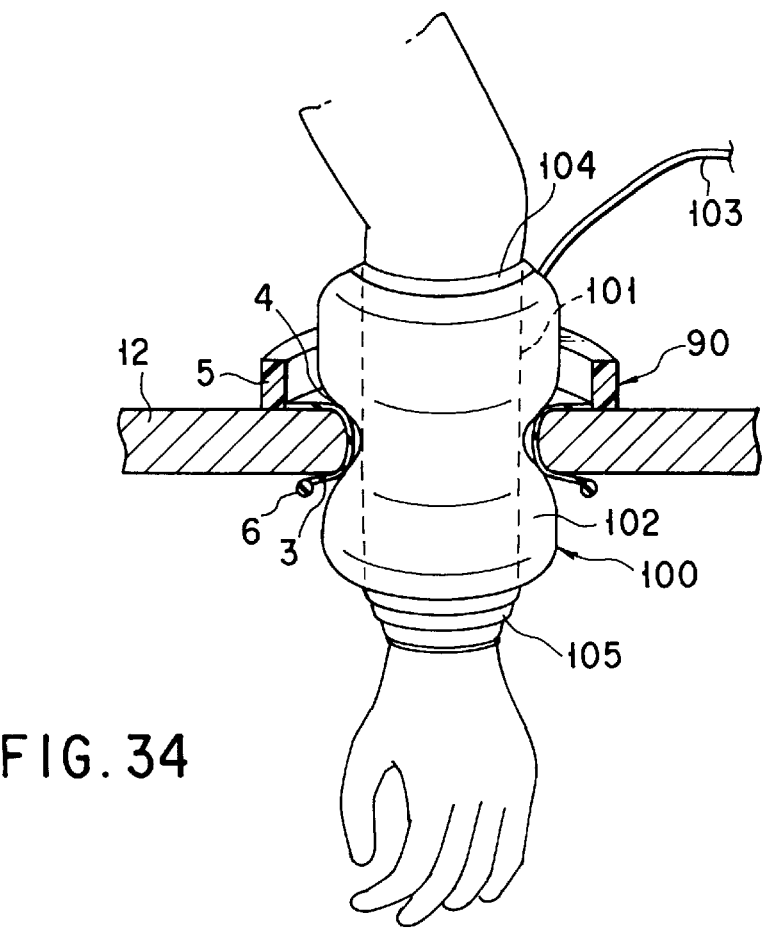
FIG. 34 is a sectional view showing another state in which an arm on which the sleeve is attached is inserted into the inside of the body through the access device.

FIG. 34 shows a state in which the arm attached with the sleeve 100 is introduced into the inside of the body in the state in which a fluid is injected into a space between the thin film 102 and the main body 101 through the tube 103 to swell the thin film 102. In the process of introducing the arm attached with the sleeve 100 into the inside of the body, the swollen part of the thin film 102 is deformed so that the inside surface of the access device 90 and the outside surface of the sleeve 100 adhere to each other. Consequently, it never happens that gas inside of the body leaks to the outside of the body. As a consequence, the air-tight state can be sufficiently held even if the first valve 4 is not provided thereon. In this case, it is desired that a unit is connected for the control of the pressure in the midst of the tube 103 in order to obtain a secured sealing effect without pushing open the inside surface (namely sectioned part) of the access device 90 to an extent more than needed with the result that the pressure of the fluid which is injected into the space between the thin film 102 and the main body 101 is held on a constant level. Furthermore, since the form of the main body 101 does not change with the swelling of the thin film 102, the arm which is inserted into the inside of the main body 101 is not fastened with the swelling of the thin film 102.

Figure 35:
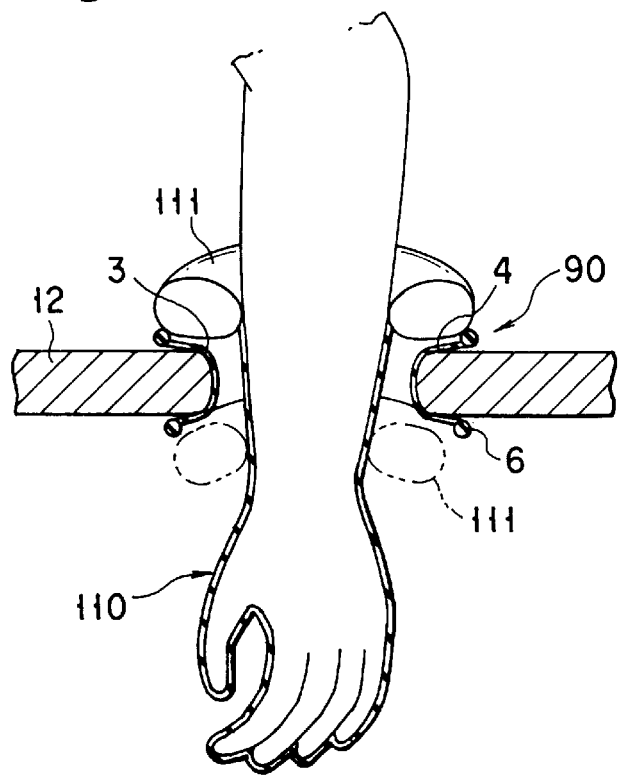
FIG. 35 is a sectional view showing a state in which an arm on which the gloves for the operation is attached is inserted into the inside of the body through the access device.

FIG. 35 shows a state in which the arm attached with the gloves 110 for operation is introduced into the inside of the body through the access device 90. As shown in FIG. 35, the gloves 110 for operation have a donut-shaped balloon 111 at an inlet part thereof. The portion of the gloves 11 for operation located between the wrist and the balloon 111 is formed of a material having an expandability and a sufficient strength.

Figure 36:
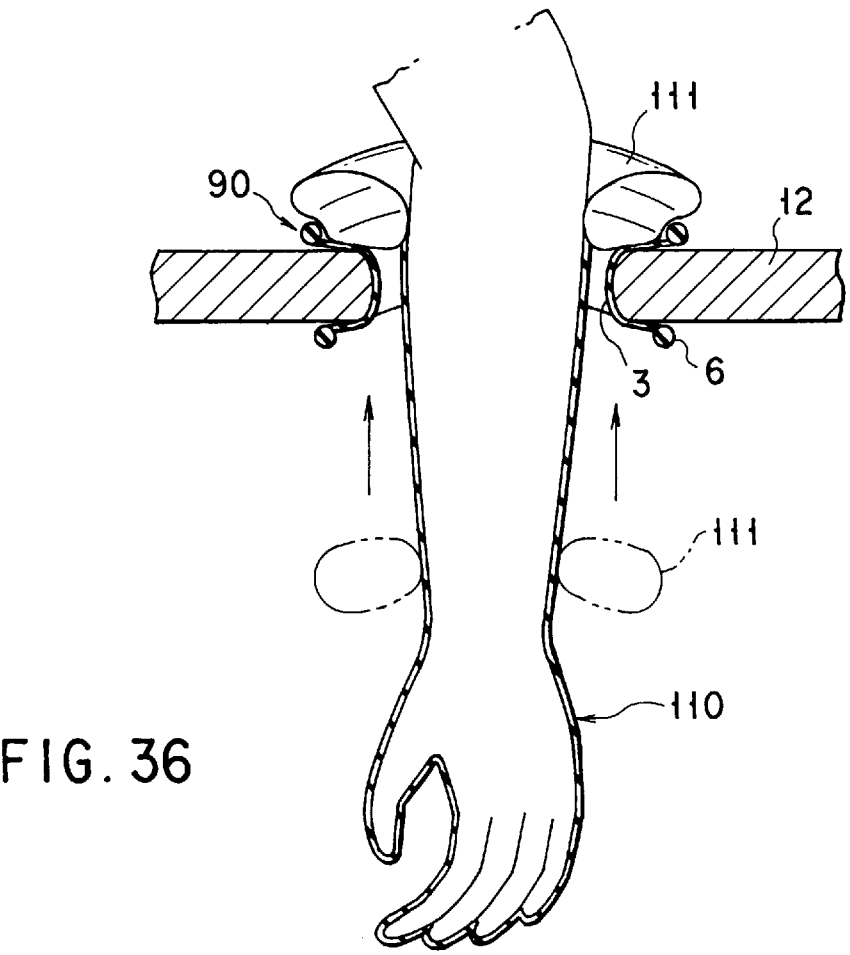

The balloon 111 is located at a position somewhat higher than the wrist as shown by a dot line in FIG. 34 in the state in which the gloves 110 for operation are attached on the arm. In the state of FIG. 35 in which the gloves 110 for operation are inserted into the access device 90 together with the arm, the balloon 111 is pressed against the first valve 4 so that the air-tight state in the abdominal cavity is held, and at the same time, the portion of the gloves 110 for operation located between the wrist and the balloon 111 is expanded. When the arm is further inserted into the back of the abdominal cavity from the state shown in FIG. 35, as shown in FIG. 36 the portion of the gloves 110 for operation located between the wrist and the balloon 111 is further expanded while the pressed state of the balloon 111 and the first valve 4 is held.

Figure 37:
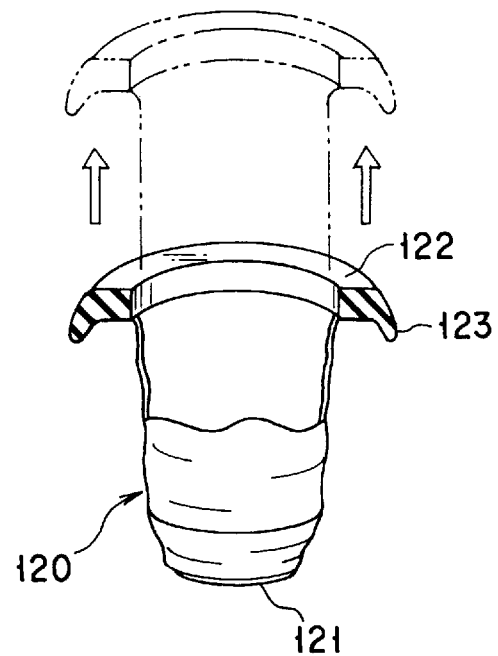
FIG. 37 is a view showing another structure of the sleeve attached on the arm.

FIG. 37 shows another structure of the sleeve attached on the arm. As shown in FIG. 37, the sleeve 120 comprises a tube-like body which is formed of a material excellent in expandability. The end part 121 of the sleeve 120 attached on the wrist is formed in a configuration somewhat thinner than the other part. On the base end part of the sleeve 120, a ring member 121 formed of an elastic material is provided. On the ring member 122, a projection 123 which is expanded toward the end side of the sleeve 120 is formed.

The sleeve 120 having such a structure is attached on the arm, and is introduced into the inside of the body together with the arm through the access device according to each of the aforementioned embodiments. In such a case, the ring member 122 adheres to the body wall, and serves as a sealing member for preventing the leakage of the gas in the abdominal cavity to the outside.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

I claim:

1. An access device for connecting an interior of a living body to the exterior thereof and for inserting an object into the living body in a sealed state, said device comprising:

a communication body to be set in tight contact with an incised part of a wall of the living body, for pushing open the incised part, thereby to allow an interior of the living body to communicate with the exterior of the living body;

a first valve attached and sealed to communication body; and a second valve attached and sealed to the communication body and adapted to be placed inside or outside the living body, said second valve being located closer to the living body than the first valve while placed outside the living body;

wherein the first valve has a valve main body made of an elastic material and an insertion part provided on the valve main body, capable of elastically deforming when the object is inserted into the insertion part, thereby to allow the object to be inserted into the living body in the sealed state, and the second valve has a plurality of film bodies formed of an elastic material and attached on an inside surface of the communication body, each of the film bodies has a contact surface, is bent toward the interior of the living body approximately in the axial direction of the communication body and is adapted to contact the adjacent film bodies at the contact surface.

2. The access device according to claim 1, wherein the contact surfaces of each film body of the second valve adheres to each other with the action of the pressure in the abdominal cavity.

3. The access device according to claim 1, wherein the communication body comprises a thin-film-like sleeve which is formed of an elastic material.

4. The access device according to claim 1, further comprising a connection tube for connecting the first valve and the communication body to separate the first valve from the communication body.

5. The access device according to claim 4, wherein the connection tube is formed in a bellows-like configuration.

6. The access device according to claim 1, wherein a thick part which is thicker than the thickness of the film body is formed at a bent end part of the film body which forms a second valve.

7. The access device according to claim 1, wherein the first and the second valve are separated from each other in a predetermined distance so that the second valve is opened with the object after the object is inserted into the insertion part of the first valve and the insertion part is closed in the sealed state.

8. The access device according to claim 1, wherein the communication body has a first support part which closely adheres to an outside surface of the wall of the living body and a second support part which closely adheres to an inside surface of the wall of the living body and which sandwiches the wall of the living body with the first support part.

9. The access device according to claim 8, wherein the first valve is attached on the first support part.

10. The access device according to claim 9, wherein the first valve can be detached from the first support part.

11. The access device according to claim 8, wherein at least one of the first and the second support part is formed of a material which can be elastically deformed.

12. The access device according to claim 11, wherein at least one of the first and the second support part is formed in an oblong configuration.

13. The access device according to claim 8, wherein the first support part has a balloon which contacts the outside surface of the wall of the living body and can be swollen and shrunken, and the balloon is swollen to be pressed against the wall of the living body in a sealed state.

14. The access device according to claim 13, wherein the balloon is swollen by the infiltration of a fluid into the inside thereof.

15. The access device according to claim 8, wherein the first valve is formed of a ring-like balloon which can be swollen and shrunken.

16. The access device according to claim 15, wherein the first support part has a balloon part which contacts the outside surface of the wall of the living body and can be swollen and shrunken, and the balloon part is swollen to be pressed against the wall of the living body in a sealed state.

17. The access device according to claim 16, wherein the inside of the balloon and the inside of the balloon part are communicated to each other through a plurality of holes.

18. The access device according to claim 1, wherein the communication body comprises a sleeve which is formed of an elastic material, a first support part which is attached on one end side of the sleeve and closely adheres to the outside surface of the wall of the living body, and a second support part which is attached on the other end side of the sleeve, closely adheres to the inside surface of the wall of the living body and sandwiches the wall of the living body with the first support part, and the sleeve. is detachably attached on the first support part.

19. The access device according to claim 1, wherein the communication body has a removal prevention ring which closely adheres to the inside surface of the wall of the living body and prevents the removal from the incised part.

20. The access device according to claim 1, further comprising means for forcibly bringing film bodies which forms a second valve into contact with each other.

21. The access device according to claim 20, wherein means for forcibly bringing the film bodies which form the second valve into contact with each other is formed of a magnet which is provided on a contact surface of each of the film bodies.

22. The access device according to claim 1, wherein a plurality of ribs are provided on a rear surface of the film bodies which form the second valve, including a rear side part of the contact surface.

23. The access device according to claim 1, wherein the first valve is formed of a ring-like balloon which can be swollen and shrunken.

24. The access device according to claim 1, wherein the main body of the first valve is formed of a plurality of thin films, and each of the thin films is arranged in such a manner that the films are overlapped with each other in an approximately central part of the first valve.

25. The access device according to claim 1, wherein the first valve has a sticking surface and is stuck to and fixed on the outside surface of the wall of the living body through the use of the sticking surface.

26. The access device according to claim 1, further comprising connection means for connecting a treatment tool which is introduced into the living body to a device outside of the living body.

27. The access device according to claim 1, wherein the object to be inserted comprises at least one glove for operation, and the glove has a main body to which the hand is inserted and an arm insertion part to which the arm is inserted, a treatment part for treating the living body is attached at a portion of the main body to which a fingers of the hand are inserted, and either an electric cord or a tube which is connected to the treatment part is integrally attached on the arm insertion part, either the electric cord or the tube is extended to the outside from an open part at the hand of the arm insertion part.

28. The access device according to claim 27, wherein the treatment part is formed of at least one of a high frequency electrode, a swab, a suction and irrigation tube, a catheter, an injection needle, and a CCD.

29. The access device according to claim 27, wherein either the electric cord or the tube which is extended to the outside from the open part at the hand of the arm insertion part is connected to one connector.

* * * * *

UNITED STATES PATENT AND TRADEMARK OFFICE
CERTIFICATE OF CORRECTION

PATENT NO.    : 6,033,426
DATED         : March 7, 2000
INVENTOR(S)   : Kunihide Kaji It is certified that error appears in the above-identified patent and that said Letters Patent is hereby corrected as shown below:

<u>Title page,</u>
Item [56], References Cited, U.S. PATENT DOCUMENTS,
delete "5,853,395  12/1998   Crook et al…..604/174";
delete "5,906,577  5/1999    Bean et al …..600/207".

Signed and Sealed this

Twenty-sixth Day of November, 2002

Attest:

Attesting Officer

JAMES E. ROGAN
*Director of the United States Patent and Trademark Office*